United States Patent
Okuda et al.

(10) Patent No.: US 11,078,470 B2
(45) Date of Patent: Aug. 3, 2021

(54) NUCLEOSIDASE

(71) Applicants: AMANO ENZYME INC., Nagoya (JP); SUNTORY HOLDINGS LIMITED, Osaka (JP)

(72) Inventors: Keita Okuda, Kakamigahara (JP); Toru Katase, Kakamigahara (JP); Yuko Kuritani, Kakamigahara (JP); Naoki Matsumoto, Tokyo (JP); Tomoko Fujimura, Fuchu (JP); Ikuma Mizuguchi, Fuchu (JP); Takako Inui, Mishima-gun (JP)

(73) Assignees: AMANO ENZYME INC., Nagoya (JP); SUNTORY HOLDINGS LIMITED, Osaka (JP)

( * ) Notice: Subject to any disclaimer, the term of this patent is extended or adjusted under 35 U.S.C. 154(b) by 0 days.

(21) Appl. No.: 16/325,952

(22) PCT Filed: Aug. 15, 2017

(86) PCT No.: PCT/JP2017/029389
§ 371 (c)(1),
(2) Date: Feb. 15, 2019

(87) PCT Pub. No.: WO2018/034289
PCT Pub. Date: Feb. 22, 2018

(65) Prior Publication Data
US 2019/0177712 A1 Jun. 13, 2019

(30) Foreign Application Priority Data

Aug. 18, 2016 (JP) ............................. JP2016-160899

(51) Int. Cl.
| C12N 9/24 | (2006.01) |
| C12N 15/00 | (2006.01) |
| C12N 1/20 | (2006.01) |
| C12N 15/09 | (2006.01) |

(52) U.S. Cl.
CPC ............ *C12N 9/2497* (2013.01); *C12N 9/24* (2013.01); *C12N 15/09* (2013.01); *C12Y 302/02001* (2013.01)

(58) Field of Classification Search
CPC ............................ C12N 9/2494; C12N 9/2497
See application file for complete search history.

(56) References Cited

U.S. PATENT DOCUMENTS 6,066,484 A * 5/2000 Hatanaka .................. C12C 5/00
435/196

FOREIGN PATENT DOCUMENTS

| EP | 0753572 A1 | 1/1997 |
| EP | 0825261 A2 | 2/1998 |
| JP | 2004-113189 A | 4/2004 |
| JP | 3824326 B2 | 9/2006 |
| JP | 3824353 B2 | 9/2006 |
| WO | 2018/066617 A1 | 4/2018 |

OTHER PUBLICATIONS

Studer. Residue mutations and their impact on protein structure and function: detecting beneficial and pathogenic changes. Biochem. J. (2013) 449, 581-594.*
Nielsen. MDYO01000001.1. GenBank. Mar. 2017.*
The List of NBRC Culture Collection Fungi:P [online], retrieval date Nov. 7, 2017, <URL https://www.nite.go.jp/nbrc/list/alphabet/03_P.html>, 15 pages. (cited in the ISR).
International Search Report dated Nov. 14, 2017, issued for PCT/JP2017/029389.
Database UniProt [Online] Jul. 22, 2015, "SubName: Full=Putative Nucleoside hydrolase {ECO:0000313 / EMBL: CE058964.1}", XP002796453. (cited in the Jan. 13, 2020 Search Report issued for EP17841511.3).
Database UniProt [Online] Apr. 16, 2014, "SubName: Full=Inosine/uridine-preferring nucleoside hydrolase domain {ECO:0000313 / EMBL:CDM38482}", XP002796454. (cited in the Jan. 13, 2020 Search Report issued for EP17841511.3).
Database Geneseq [Online], May 31, 2018, "Penicillium multicolor PN1 protein, SEQ ID 1.", XP002796455. (cited in the Jan. 13, 2020 Search Report issued for EP17841511.3).
Database Geneseq [Online], May 31, 2018, "Penicillium multicolor PN2 protein, SEQ ID 2.", XP002796456. (cited in the Jan. 13, 2020 Search Report issued for EP17841511.3).
Database UniProt [Online], Jun. 7, 2017, "RecName: Full=IU_nuc_hydro domain-containing protein {ECO:0000259: Pfam:PF01156}", XP002796457. (cited in the Jan. 13, 2020 Search Report issued for EP17841511.3).
Supplementary European Search Report dated Jan. 13, 2020, issued for the European patent application No. 17841511.3.

* cited by examiner

Primary Examiner — Yong D Pak
(74) Attorney, Agent, or Firm — Locke Lord LLP

(57) ABSTRACT

It is an object of the present invention to provide a novel enzyme useful for producing low-purine foods or beverages. There is disclosed a nucleosidase comprising an amino acid sequence of SEQ ID NO: 1 or an amino acid sequence having 85% or more identity with the amino acid sequence, or an amino acid sequence of SEQ ID NO: 2 or an amino acid sequence having 88% or more identity with the amino acid sequence.

8 Claims, 24 Drawing Sheets
Specification includes a Sequence Listing.

|  | Peak 1 | Peak 2 | Peak 3 |
|---|---|---|---|
| SDS-PAGE molecular weight — Sugar chain present | About 50 kDa | About 50 kDa | About 53 kDa |
| SDS-PAGE molecular weight — Sugar chain absent | About 40 kDa | About 40 kDa | About 48 kDa |
| Gel filtration molecular weight | About 230 kDa | About 230 kDa | About 126 kDa |
| N-terminal amino acid sequence | ADKHYAIMDNDWYTA | ADKHYAIMDNDWYTA | VETKLIFLT |
|  | SEQ ID NO: 7 | SEQ ID NO: 8 | SEQ ID NO: 9 |

*Fig. 7*

| Probe sequence | PN1 | GAGGATCCCGAAACCTTCCTACGTGTCAAGGAGGTCGTTGTGATGGGTGGAGCAATCAACCAGCCTGGAAATGTATGAACCCGTCG AAACACCGATTTGATAATAAGTCATTAACCGCGATTGACTAGGTCACCCCCGTTGACTAGGAATTCAACGCCTAACGGAGACGGCCGTTGCA GCTGCGGGAGTCTTTGCGGTGACATCGACTCTGCGTCTCTTCCCGCTGGACATCACCCTGCGCACTAACCTGTCCCGGGCCAATTCCGCCAAGCA AAGCTCAGCGCGACAATTGACTCTGCGTCTCTTCCCGCTGGACATCACCCTGCGCACTAACCTGTCCCGGGCCAATTCCGCCAAGCA GTTGAGGCTCTCCTCGGAACAGGGCTCACCCGTCGGCTGAATGGGTGACAGATTCATGGACACACGTTCCGAACCCTGGAACGCCTG CACCCGGCCATGAGGGCGATGAAGCCCAGCTGAGTCTCCACGACCCTGTCTGTGTATGCCCTTACAGCAGAGGATTCGCAC TGGACTCCCTCCGGCCAATTCCCCAGAGGACATTCGTGTTGAGAGACATTGGGCC SEQ ID NO: 18 |
|---|---|---|

| Probe sequence | PN2 | AGACACCGCAAACACCTGGCAGCCTCAGGTGCGCTCTGCACGGTGCTCTGCAACCTGGAACTTGAGCTGTATCCCGGTTTA CCCAGGTCGACATGGCCGCTCATCAACACCCCCAAACCGGTTCCAGGCGTTCATGGCAAGCTGCCATGGCAGGGGTGC TTTTGGCCGGAGAACAAGACTCTCGAGGCGGTAACGATCCTACCGCCAACCGTATCGTCAAGGCCGCTTCAA GGAAGGGTTCCCAAGGCAAGCCCGAGAACAGAACAATCTGCTGCCGGTCGGCATGATGCCCAGTTTGCATCTCTGGCTAAGGAGTTGGT CTCGATCTACTCTGCTGGAGCCTGACCAATGTTGCGCTGGCCATGGATGAATCCCCAGTTTGCATCTCTGGCTAAGGAGTTGGT TATCATGGGTGGATACGTCGATTTGAATATGCTCCAGGCCACTGGAAGTGTCTTGCTGATGTCTTCAATCTG SEQ ID NO: 19 |
|---|---|---|

Fig. 8

| | PN1 |
|---|---|
| Genomic sequence (SEQ ID NO: 4) | ATGGCACCTAAGAAAATCATCATTGACACTGACCCGGTAAGTTGCCTATACATAACTGAAGATATCTACTCCTAGACATG CTAATGAATGATTAGGGTATCGATGACATCCTGGCACTGCTGCTGGCTCTGTCATCTAAGCCAGAGGATGTTGAGATTCT ACTTATCTCTTTAACATTTGGAAACATTGAGGTGAAGAAGTGAGTGCTACCTTTGTGAAAGTCAACTCAGAAACGAGTTC AGCCTATTTATTTCCTTAGAGCTGTCTTGGAAATGTGGTCTCCATGTTTCATATCCTCGAGCGCGAGATCCAGTGGCGTC GTGGTAACGGCAAGTCCGAAGGGTATGGCACTATGCGTGCTTTCCGCCCAGTAGTAGCCGTGGGAGCGGAAGATCCCTTG GAAGACCAGAAGATGCTCGCTGATTATTTCCGTAAGTGCTTTGTGGTTTTTGAAAGTCAATCACGTCGCTGAGAATTACCC CGCAGATGGAACGATGGCCTTGGTGGCATCCATGCTAGTGTAGGCTAAACGCCCACCTTATTCGACCAATGATGTACCC ATTTTGTAACACTATCTGGACAGGACCCACATCTCACTCCAAGCAAGGCCTGGGAGCATCTATTCACCCCGGCCGTGGAT CCCCAGGGGATCGAGCCTGTGCAAACGGGAGCTGGTCCGGCGACCATTCCTTTATCCCATCAAGACTACCTGCACACAA GGAGATTCTTCGTGCACTGCGCCAGAATGAGCCTGACACCGTGACTCTCGTGGCGGTTGGTCCACTGACCAACTTGGCCT TGGCAGCAGCAGAGGATCCCGAAACCTTCCTACGTGTCAAGGAGGTCGTTGTGATGGGTGGAGCAATCAACCAGCCTGGA AATGTATGAAGCGCGTCGAAACACCCATTTGATAATAAGTCATTAACCGCGATTGACTAGGTCACCCCCGTTGGAGAATT CAACGCCTACGCAGACGCCGTTGCAGGTGCGGAGTCTTTGCGCTGACATCACCTAATCCCAACTCGACTCTACGCACCGA CCACGAGTCCACTACTTGGCCTGTACCCTGCAAAGCTCAGCCGACAATTGACTCTGCGTGTCTTCCCGCTGGACATGACC CTGCGCCATAACCGTGTCCGCGCGGCCAATTCCGCCAAGCAGTTGAGCCTCTCCTCGCAACAGGCTCACCCCTCGCTGAATG GGTGACAGGCATTCATGGACACACGTTCCGAACCCCTGGAACGCCTGCACCCCGGCCATGAGGGCGATGAAGCCCAGCTGA GTCTCGACGACCCTGTCTGTGTGTGGTATGCCCTTACAGCAGAGGATTCGCACTGGACTCCCTCCGCCAATTCCCAGAG GACATTCGTGTTGAGACATTGGGCCAGTGGACGCGTGGTATGTGCGTAATCGATGGCCGAAACCGCCATAAGATTGATGG CGACGAGGAAAGCTCGAGTGATCATGGTCTGTGGTTGAGTGCTCGTGCAGGAAACCGCATTTTGCGAATGGATGGATCGC CAGCCGAACACACGTTCGGCAAGATCCTCATCGATAGAATCTTCCACTAA |
| | PN2 |
| Genomic sequence (SEQ ID NO: 6) | ATGCATTTCCCTGTTTCATTGCCGCTGTTGTGCGGCTCTTTGCTGCCTCTCATCACCGGCACCCTGGCAGTGCCCAAGGC CTCGCGTGCCGACAAGGACTATGCCATCATGGACAATGATTGGTACACAGCGGGGTTTCGTGCCTTACCTGATCGCCCTCG ATGGGATGTGGAGTTCTGGGCCTAGCCTCTGGTTAGTGTTGATCCGCATCCATACCGGTTTCCTTCAAGGTCTGCAG TGCTAACTTCCATGTCATATCAGACACGGCAAACACCTGGCAGCCTCAGGTCGCTCTGCACGGCTGTCGCAACTCTGGAAG CTGGCAACTTGAGCTGTATCCCCGTTTACCCAGGCTCGACATGGCCGCTCATCAACACCGCCAACGGCTTCCAGGCGTGG GAAATGGTTCATGGCAAGGTGCCATGGGAGGGTGCTTTTGCGCCGGAGAACAAGACTCTCGACGCCGAGGTAACGATCG TACCTGTGGGCAACCGACGTATCGTCAAGGCCGCTTCAAGGAAGGGTTCGCCAAGGGCAAGCCCGGAAACAGAACAT CTGCTGGCCAACTTCATGGTCGACATGGTGCACAAGTACCCCGGCCAGGTCTCGATCTACTCTGCTGGAGCCCTGACCAAT GTTGGCGCTGGCTGTGCGGCATGGATCCCCAGTTTGCATCTCTGGGCTAAGGAGTTGGTTATCATGGGTGGATACGTCGATTT GAATAGCTCCAGGCCACTGGAAGTGTCTTGCTGGCTGATGTTCAATCTCATGTATGTTTCATTCCCGGCTTCTATCAGG TGTGTTCATCTGCTAACTTCTCTTTAGATCAACTTGATGATTCATCCCGAGGCCTCCAAGATCGCATTGACTGCCGAATT CCCCAATATCGACCATCGCGGGTAACGTCGCCAACCAGGTCTTTCCTACCAAGGAGTTCGTCGACGAGATCGCCTCGGTTC CAAACGCCTACAGGAAGCTCTTCCACGACTACTACGATCTGTCCTTCCCCTTCTGGGATGAGACGGCTGCCGCGCTGATG GTTGACCCTACTCTTGGTACCAACCAGACCTCTGGTGAGTTTAATCTCGGCATTGACACTTGTATGAACAAATCTAACAGC TTATAGTCTTCCTCGACGTGATACCGCTTATGGTAGCCCCAACTATGGTAACATTCACGTTTACCGACAACGGTCTTGCC CCTGTTGGTATCGGGAGGTCAACTTTGTCTTCCAGGTTGATGGGGATAGACTTAAGCAGCGCATCAAGCACTCTCTGCA GTACGGCAAGTCATGCGCGGACCTGAGAAATGAGCGTTGA |

*Fig. 9*

| | PN1 |
|---|---|
| cDNA sequence (SEQ ID NO: 3) | ATGGCAGGTAAGAAAATCATCATTGACAGTGAGCCGGGTATCGATGAGATCCTGGCACTGGTGCTGGCTCTGTCATGTAA<br>GCCAGAGGATGTTGAGATTCTACTTATCTCTTTAACATTTGGAAACATTGAGGTGAAGAACTGTCTTGAAATGTGGTCT<br>CCATGTTTCATATGCTCGAGCGCGAGATCCAGTGGCGTCGTGGTAACGGCAAGTCCGAAGGCTATGGCACTATGCGTGCT<br>TTCGGCCCAGTAGTAGCCGTGGGAGCGGAAGATCCCTTGGAAGACCAGAAGATGCTCGCTGATTATTTCCATGGAACCGA<br>TGGCCTTGGTGGCATCCATGCTAGTCACCCACATCTCACTCCAAGCAAGGCCTGGGAGCATCTATTCACCCCGGCCGTGG<br>ATCCCCAGGGGATCGAGCCTGTGCAAACGGGAGCTGGTGCGGCGACCATTCCTTTATCCCATGAAGACTACCTGCACAG<br>AAGGAGATTCTTCGTGCACTGCGCCAGAATGAGCCTGACACCGTGACTCTCGTGGCGGTTGTCCACTGACCAACTTGGC<br>CTTGGCAGCAGGAGGATCCCGAAACCTTCCTACGTGTCAAGGAGGTCGTTGTGATGGGTGGAGCAATCAACCAGCCTG<br>GAAATGTCAGCCCGCGTTGGAGAATTCAAGGCCTACGCAGACGCCGTTGCAGCTGCGCGAGTCTTTGGCGTGACATCACCT<br>AATCCCAACTCGACTCTACCACCGACCACGAGTCCACTAGTTGGCCTGTACCCTGGAAAGCTCAGCCGACAATTGACTCT<br>GCGTCTCTTCCCGCTGGACATCACCCTGCCGCATAACCGTCCCGCGGCCAATTCCGCCAAGCAGTTGAGCCTCTCCTCG<br>CAACAGGCTCACCCCTCGCTGAATGGGTGACAGCATTCAGGCACACACGTTCCGAACCCTGGAACGCCTGCACGCCGGC<br>CATGAGGGCGATGAAGCCCAGCTGAGTCTCCACGACCCTGTCTGTGTGTGGTATGCCCTTACAGCAGAGGATTCGCACTG<br>GACTCCCTCCGCCAATTCCCCAGAGGACATTCGTGTTGAGACATTGGGCCAGTGGACGCGTGGTATGTGCGTAATCGATG<br>GCCGAAACCGCCATAAGATTGATGGCGACGAGGAAAGCTCGAGTGATCATGGTCTGTCGTTGAGTGCTCGTGCAGGAAAC<br>CGCATTTTGCGAATGGATGGATCGCCAGCCGAACACACGTTCGGCAAGATCCTCATCGATAGAATCTTCCACTAA |
| | PN2 |
| cDNA sequence (SEQ ID NO: 5) | ATGCATTTCCCTGTTTCATTGCCGCTGTTGTGCCGCTCTTTGCTGCCTCTCATCACGGCACCCTGGCAGTGCCCAAGGC<br>CTCGCGTGCCGACAAGCACTATGCCATCATGGCCGGCAAAGATTGGTACACAGCGGGGTTTCGTGGCTTAGGTGATCGGCCCTCG<br>ATGGCGATGTGGAGGTTCTGGGCCTAGCCTCTGACACCGCAAACACCTGGCAGGCTCAGGTCGCTCTGCACGCTGTCGCA<br>ACTCTGGAAGCTGGCAACTTGAGCTGTATCCCCCTTTACCCAGGCTCGACATGGCCGCTCATCAACACCCCCAACCGCTT<br>CCAGGCGTGGGAAATGGTTCATGGCAAGCTGCCATGGGAAGGGTGCTTTTGCGCCGGAGAACAAGACTCTCGAGGCCGAGG<br>GTAACGATCCTACCTCTGGCAACCCCAACCGTATCGTCAAGGCCGCTTTCAAGGAAGGGTTCCCAAGGGCAAGCCCGAC<br>AACAGAACATCTGCTGCCAACTTCATGGTCGAGATGGTGCACAAGTACCCGGCCAGGTCTCGATCTACTCTGCTGGAGC<br>CCTGACCAATGTTGCGCTGGCTGTGCGCATGGATCCCCAGTTTGCATCTCTGGCTAAGGAGTTGGTTATCATGGGTGGAT<br>ACGTCGATTTGAATATGCTCCAGGCGCACTGGAACTGTCTTGCTGGCTGATGCTTCAATCTGATATCAACTTGATGATTGAT<br>GCCGAGGCCTCCAAGATCGCATTGACTGCCGAATTCCCAATATCACCATCGCCGGTAACGTCGCCAACCAGGTCTTTCC<br>TACCAAGGAGTTCGTCGACGAGATCGCCTCCGTTCCAAACCCCTACAGCAAGCTCTTCCAGGACTACTACGATCTGTCCT<br>TCCCCTTCTGGGATGAGACGGCTGCCGCGCTGATGGTTGACCCTACTCTTGCTACCAACCAGACCTGTGTCTTCCTCGAC<br>GTGGATACCGCTTATGGTAGCCCAACTATGGTAACATTCACGTTTACCAGAAGGCTCTTGCCCCTGTTGGTATCGGGA<br>GGTCAACTTTGTCTTCCAGGTTGATGGGGATAGACTTAAGGAGCGGATCAAGCACTCTCTGCAGTACGCCAAGTCATGCC<br>CCGACCTGAGAAATGAGCGTTGA |

*Fig. 10*

PN1 (peak 3) (SEQ ID NO: 1)

MAPKKIIIDTDPGIDDILALLLALSSKPEDVEILLISLTFGNIEVKNCLRNVVSMFHILE
REIQWRRGNGKSEGYGTMRAFRPVVAVGAEDPLEDQKMLADYFHGTDGLGGIHASHPHLT
PSKAWEHLFTPAVDPQGIEPVQTGAGPGDHSFIPSRLPAHKEILRALRQNEPDTVTLVAV
GPLTNLALAAAEDPETFLRVKEVVVMGGAINQPGNVTPVGEFNAYADAVAAARVFALTSP
NPNSTLPPTTSPLLGLYPAKLSRQLTLRLFPLDITLRHNLSRGQFRQAVEPLLATGSPLA
EWVTAFMGHTFRTLERLHPGHEGDEAQLSLHDPVCVWYALTAEDSHWTPSANSPEDIRVE
TLGQWTRGMCVIDGRNRHKIDGDEESSSDHGLWLSARAGNRILRMDQSPAEHTFGKILID
RIFH*

PN2 (peaks 1 and 2) (SEQ ID NO: 2)

MHFPVSLPLLCGSLLPLITGTLAVPKASRADKHYAIMDNDWYTAGFVPYLIALDGDVEVL
GLASDTANTWQPQVALHAVATLEAGNLSCIPVYPGSTWPLINTPNRFQAWEMVHGKLPWE
GAFAPENKTLEAEGNDPTSGNPNRIVKAAFKEGFPKGKPENRTSAANFMVEMVHKYPGGV
SIYSAGALTNVALAVRMDPQFASLAKELVIMGGYVDLNMLQATGSVLLADLQSDINLMID
PEASKIALTAEFPNITIAGNVANQVFPTKEFVDEIASVPNPYSKLFHDYYDLSFPFWDET
AAALMVDPTLATNQTSVFLDVDTAYGSPNYGNIHVYQKALAPVGIREVNFVFQVDGDRLK
QRIKHSLQYPKSCADLRNER*

*Fig. 11*

|  | PN1 | PN2 |
|---|---|---|
| Number of bases (cDNA) | 1,275 bp | 1,143 bp |
| Number of introns | 5 | 3 |
| Amino acid length | 424 aa | 380 aa |
| Estimated molecular weight | 46,400 | 41,600 |
| Estimated pI | 5.7 | 5.0 |

*Fig. 12*

SEQUENCE LISTING

```
<160> NUMBER OF SEQ ID NOS: 19

<210> SEQ ID NO 1
<211> LENGTH: 424
<212> TYPE: PRT
<213> ORGANISM: Penicillium multicolor

<400> SEQUENCE: 1

Met Ala Pro Lys Lys Ile Ile Ile Asp Thr Asp Pro Gly Ile Asp Asp
1               5                   10                  15

Ile Leu Ala Leu Leu Leu Ala Leu Ser Ser Lys Pro Glu Asp Val Glu
            20                  25                  30

Ile Leu Leu Ile Ser Leu Thr Phe Gly Asn Ile Glu Val Lys Asn Cys
        35                  40                  45

Leu Arg Asn Val Val Ser Met Phe His Ile Leu Glu Arg Glu Ile Gln
    50                  55                  60
```

Trp Arg Arg Gly Asn Gly Lys Ser Glu Gly Tyr Gly Thr Met Arg Ala
 65                  70                  75                  80

Phe Arg Pro Val Val Ala Val Gly Ala Glu Asp Pro Leu Glu Asp Gln
                 85                  90                  95

Lys Met Leu Ala Asp Tyr Phe His Gly Thr Asp Gly Leu Gly Gly Ile
            100                 105                 110

His Ala Ser His Pro His Leu Thr Pro Ser Lys Ala Trp Glu His Leu
        115                 120                 125

Phe Thr Pro Ala Val Asp Pro Gln Gly Ile Glu Pro Val Gln Thr Gly
    130                 135                 140

Ala Gly Pro Gly Asp His Ser Phe Ile Pro Ser Arg Leu Pro Ala His
145                 150                 155                 160

Lys Glu Ile Leu Arg Ala Leu Arg Gln Asn Glu Pro Asp Thr Val Thr
                165                 170                 175

Leu Val Ala Val Gly Pro Leu Thr Asn Leu Ala Leu Ala Ala Ala Glu
            180                 185                 190

Asp Pro Glu Thr Phe Leu Arg Val Lys Glu Val Val Met Gly Gly
        195                 200                 205

Ala Ile Asn Gln Pro Gly Asn Val Thr Pro Val Gly Glu Phe Asn Ala
    210                 215                 220

Tyr Ala Asp Ala Val Ala Ala Arg Val Phe Ala Leu Thr Ser Pro
225                 230                 235                 240

Asn Pro Asn Ser Thr Leu Pro Pro Thr Thr Ser Pro Leu Leu Gly Leu
                245                 250                 255

Tyr Pro Ala Lys Leu Ser Arg Gln Leu Thr Leu Arg Leu Phe Pro Leu
            260                 265                 270

Asp Ile Thr Leu Arg His Asn Leu Ser Arg Gly Gln Phe Arg Gln Ala
        275                 280                 285

Val Glu Pro Leu Leu Ala Thr Gly Ser Pro Leu Ala Glu Trp Val Thr
    290                 295                 300

Ala Phe Met Gly His Thr Phe Arg Thr Leu Glu Arg Leu His Pro Gly
305                 310                 315                 320

His Glu Gly Asp Glu Ala Gln Leu Ser Leu His Asp Pro Val Cys Val
                325                 330                 335

Trp Tyr Ala Leu Thr Ala Glu Asp Ser His Trp Thr Pro Ser Ala Asn
            340                 345                 350

Ser Pro Glu Asp Ile Arg Val Glu Thr Leu Gly Gln Trp Thr Arg Gly
        355                 360                 365

Met Cys Val Ile Asp Gly Arg Asn Arg His Lys Ile Asp Gly Asp Glu
    370                 375                 380

Glu Ser Ser Ser Asp His Gly Leu Trp Leu Ser Ala Arg Ala Gly Asn
385                 390                 395                 400

Arg Ile Leu Arg Met Asp Gly Ser Pro Ala Glu His Thr Phe Gly Lys
                405                 410                 415

Ile Leu Ile Asp Arg Ile Phe His
            420

<210> SEQ ID NO 2
<211> LENGTH: 380
<212> TYPE: PRT
<213> ORGANISM: Penicillium multicolor

<400> SEQUENCE: 2

Met His Phe Pro Val Ser Leu Pro Leu Leu Cys Gly Ser Leu Leu Pro
1               5                   10                  15

Leu Ile Thr Gly Thr Leu Ala Val Pro Lys Ala Ser Arg Ala Asp Lys
            20                  25                  30

His Tyr Ala Ile Met Asp Asn Asp Trp Tyr Thr Ala Gly Phe Val Pro
        35                  40                  45

Tyr Leu Ile Ala Leu Asp Gly Asp Val Glu Val Leu Gly Leu Ala Ser
 50                  55                  60

Asp Thr Ala Asn Thr Trp Gln Pro Gln Val Ala Leu His Ala Val Ala
65                  70                  75                  80

Thr Leu Glu Ala Gly Asn Leu Ser Cys Ile Pro Val Tyr Pro Gly Ser
                85                  90                  95

Thr Trp Pro Leu Ile Asn Thr Pro Asn Arg Phe Gln Ala Trp Glu Met
            100                 105                 110

Val His Gly Lys Leu Pro Trp Glu Gly Ala Phe Ala Pro Glu Asn Lys
        115                 120                 125

Thr Leu Glu Ala Glu Gly Asn Asp Pro Thr Ser Gly Asn Pro Asn Arg
130                 135                 140

Ile Val Lys Ala Ala Phe Lys Glu Gly Phe Pro Lys Gly Lys Pro Glu
145                 150                 155                 160

Asn Arg Thr Ser Ala Ala Asn Phe Met Val Glu Met Val His Lys Tyr
                165                 170                 175

Pro Gly Gln Val Ser Ile Tyr Ser Ala Gly Ala Leu Thr Asn Val Ala
            180                 185                 190

Leu Ala Val Arg Met Asp Pro Gln Phe Ala Ser Leu Ala Lys Glu Leu
        195                 200                 205

Val Ile Met Gly Gly Tyr Val Asp Leu Asn Met Leu Gln Ala Thr Gly
210                 215                 220

Ser Val Leu Leu Ala Asp Leu Gln Ser Asp Ile Asn Leu Met Ile Asp
225                 230                 235                 240

Pro Glu Ala Ser Lys Ile Ala Leu Thr Ala Glu Phe Pro Asn Ile Thr
                245                 250                 255

Ile Ala Gly Asn Val Ala Asn Gln Val Phe Pro Thr Lys Glu Phe Val
            260                 265                 270

Asp Glu Ile Ala Ser Val Pro Asn Pro Tyr Ser Lys Leu Phe His Asp
        275                 280                 285

Tyr Tyr Asp Leu Ser Phe Pro Phe Trp Asp Glu Thr Ala Ala Ala Leu
290                 295                 300

Met Val Asp Pro Thr Leu Ala Thr Asn Gln Thr Ser Val Phe Leu Asp
305                 310                 315                 320

Val Asp Thr Ala Tyr Gly Ser Pro Asn Tyr Gly Asn Ile His Val Tyr
                325                 330                 335

Gln Lys Ala Leu Ala Pro Val Gly Ile Arg Glu Val Asn Phe Val Phe
            340                 345                 350

Gln Val Asp Gly Asp Arg Leu Lys Gln Arg Ile Lys His Ser Leu Gln
        355                 360                 365

Tyr Pro Lys Ser Cys Ala Asp Leu Arg Asn Glu Arg
370                 375                 380

<210> SEQ ID NO 3
<211> LENGTH: 1275
<212> TYPE: DNA
<213> ORGANISM: Penicillium multicolor

<400> SEQUENCE: 3
atggcaccta agaaaatcat cattgacact gacccgggta tcgatgacat cctggcactg    60

```
ctgctggctc tgtcatctaa gccagaggat gttgagattc tacttatctc tttaacattt      120
ggaaacattg aggtgaagaa ctgtcttcga aatgtggtct ccatgtttca tatcctcgag      180
cgcgagatcc agtggcgtcg tggtaacggc aagtccgaag gctatggcac tatgcgtgct      240
ttccgcccag tagtagccgt gggagcgaaa gatcccttgg aagaccagaa gatgctcgct      300
gattatttcc atggaaccga tggccttggt ggcatccatg ctagtcaccc acatctcact      360
ccaagcaagg cctgggagca tctattcacc ccggccgtgg atccccaggg gatcgagcct      420
gtgcaaacgg agctggtcc cggcgaccat tcctttatcc catcaagact acctgcacac       480
aaggagattc ttcgtgcact cgccagaat gagcctgaca ccgtgactct cgtggcggtt       540
ggtccactga ccaacttggc cttggcagca gcagaggatc ccgaaacctt cctacgtgtc      600
aaggaggtcg ttgtgatggg tggagcaatc aaccagcctg aaatgtcac ccccgttgga       660 gaattcaacg cctacgcaga cgccgttgca gctgcgcgag tctttgcgct gacatcacct      720
aatcccaact cgactctacc accgaccacg agtccactac ttggcctgta ccctgcaaag      780
ctcagccgac aattgactct gcgtctcttc ccgctggaca tcaccctgcg ccataacctg      840
tcccgcggcc aattccgcca agcagttgag cctctcctcg caacaggctc acccctcgct      900
gaatgggtga cagcattcat gggacacacg ttccgaaccc tggaacgcct gcaccccggc      960
catgagggcg atgaagccca gctgagtctc acgaccctg tctgtgtgtg gtatgccctt      1020
acagcagagg attcgcactg gactccctcc gccaattccc cagaggacat tcgtgttgag     1080
acattgggcc agtggacgcg tggtatgtgc gtaatcgatg gccgaaaccg ccataagatt     1140
gatggcgacg aggaaagctc gagtgatcat ggtctgtggt tgagtgctcg tgcaggaaac     1200
cgcattttgc gaatgatgg atcgccagcc gaacacacgt tcggcaagat cctcatcgat     1260
agaatcttcc actaa                                                     1275

<210> SEQ ID NO 4
<211> LENGTH: 1016
<212> TYPE: DNA
<213> ORGANISM: Penicillium multicolor

<400> SEQUENCE: 4
gtacccattt tctaacacta tctggacagc acccacatct cactccaagc aaggcctggg       60
agcatctatt caccccggcc gtggatcccc aggggatcga gcctgtgcaa acggagctg      120 gtcccggcga ccattccttt atcccatcaa gactacctgc acacaaggag attcttcgtg     180
cactgcgcca gaatgagcct gacaccgtga ctctcgtggc ggttggtcca ctgaccaact     240
tggccttggc agcagcagag gatcccgaaa ccttcctacg tgtcaaggag gtcgttgtga     300
tgggtggagc aatcaaccag cctggaaatg tatgaacccc gtcgaaacac ccatttgata     360
ataagtcatt aaccgcgatt gactaggtca ccccgttgg agaattcaac gcctacgcag      420
acgccgttgc agctgcgcga gtctttgcgc tgacatcacc taatcccaac tcgactctac     480
caccgaccac gagtccacta cttggcctgt accctgcaaa gctcagccga caattgactc     540
tgcgtctctt cccgctggac atcaccctgc gccataacct gtcccgcggc caattccgcc     600
aagcagttga gcctctcctc gcaacaggct cacccctcgc tgaatgggtg acagcattca     660
tgggacacac gttccgaacc ctggaacgcc tgcaccccgg ccatgagggc gatgaagccc     720
agctgagtct cacgaccct gtctgtgtgt ggtatgccct tacagcagag gattcgcact      780
ggactccctc cgccaattcc ccagaggaca ttcgtgttga cattgggc cagtggacgc       840
```

```
gtggtatgtg cgtaatcgat ggccgaaacc gccataagat tgatggcgac gaggaaagct      900
cgagtgatca tggtctgtgg ttgagtgctc gtgcaggaaa ccgcattttg cgaatggatg      960
gatcgccagc cgaacacacg ttcggcaaga tcctcatcga tagaatcttc cactaa        1016

<210> SEQ ID NO 5
<211> LENGTH: 1143
<212> TYPE: DNA
<213> ORGANISM: Penicillium multicolor

<400> SEQUENCE: 5
atgcatttcc ctgtttcatt gccgctgttg tgcggctctt tgctgcctct catcaccggc       60
accctggcag tgcccaaggc ctcgcgtgcc gacaagcact atgccatcat ggacaatgat      120
tggtacacag cgggtttcgt gccttacctg atcgccctcg atggcgatgt ggaggttctg      180
ggcctagcct ctgacaccgc aaacacctgg cagcctcagg tcgctctgca cgctgtcgca      240
actctggaag ctggcaactt gagctgtatc cccgtttacc caggctcgac atggccgctc      300
atcaacaccc ccaaccgctt ccaggcgtgg gaaatggttc atggcaagct gccatgggag      360
ggtgcttttg cgccggagaa caagactctc gaggccgagg gtaacgatcc tacctctggc      420
aaccccaacc gtatcgtcaa ggccgctttc aaggaagggt tccccaaggg caagcccgag      480
aacagaacat ctgctgccaa cttcatggtc gagatggtgc acaagtaccc cggccaggtc      540
tcgatctact ctgctggagc cctgaccaat gttgcgctgg ctgtgcgcat ggatccccag      600
tttgcatctc tggctaagga gttggttatc atgggtggat acgtcgattt gaatatgctc      660
caggccactg gaagtgtctt gctggctgat cttcaatctg atatcaactt gatgattgat      720
cccgaggcct ccaagatcgc attgactgcc gaattcccca atatcaccat cgccggtaac      780
gtcgccaacc aggtctttcc taccaaggag ttcgtcgacg agatcgcctc cgttccaaac      840
ccctacagca agctcttcca cgactactac gatctgtcct tccccttctg ggatgagacg      900
gctgccgcgc tgatggttga ccctactctt gctaccaacc agacctctgt cttcctcgac      960
gtggataccg cttatggtag ccccaactat ggtaacattc acgtttacca gaaggctctt     1020
gcccctgttg gtatccggga ggtcaacttt gtcttccagg ttgatgggga tagacttaag     1080
cagcgcatca agcactctct gcagtacccc aagtcatgcg ccgacctgag aaatgagcgt     1140
tga                                                                    1143

<210> SEQ ID NO 6
<211> LENGTH: 847
<212> TYPE: DNA
<213> ORGANISM: Penicillium multicolor

<400> SEQUENCE: 6
acgatcctac ctctggcaac cccaaccgta tcgtcaaggc cgctttcaag gaagggttcc       60
ccaagggcaa gcccgagaac agaacatctg ctgccaactt catggtcgag atggtgcaca      120
agtaccccgg ccaggtctcg atctactctg ctggagccct gaccaatgtt gcgctggctg      180
tgcgcatgga tccccagttt gcatctctgg ctaaggagtt ggttatcatg ggtggatacg      240
tcgatttgaa tatgctccag gccactggaa gtgtcttgct ggctgatctt caatctgatg      300
tatgtttcat tcccggcttc tatcagctgt gttcatctgc taacttctct ttagatcaac      360
ttgatgattg atcccgaggc ctccaagatc gcattgactg ccgaattccc caatatcacc      420
atcgccggta acgtcgccaa ccaggtcttt cctaccaagg agttcgtcga cgagatcgcc      480
tccgttccaa accctacag caagctcttc cacgactact acgatctgtc cttcccttc       540
```

-continued

```
tgggatgaga cggctgccgc gctgatggtt gaccctactc ttgctaccaa ccagacctct    600
ggtgagttta atctcgcatt gacacttgta tgaacaaatc taacagctta tagtcttcct    660
cgacgtggat accgcttatg gtagccccaa ctatggtaac attcacgttt accagaacgc    720
tcttgcccct gttggtatcc gggaggtcaa ctttgtcttc caggttgatg gggatagact    780
taagcagcgc atcaagcact ctctgcagta ccccaagtca tgcgccgacc tgagaaatga    840
gcgttga                                                              847
```

```
<210> SEQ ID NO 7
<211> LENGTH: 15
<212> TYPE: PRT
<213> ORGANISM: Penicillium multicolor

<400> SEQUENCE: 7

Ala Asp Lys His Tyr Ala Ile Met Asp Asn Asp Trp Tyr Thr Ala
1               5                   10                  15

<210> SEQ ID NO 8
<211> LENGTH: 15
<212> TYPE: PRT
<213> ORGANISM: Penicillium multicolor

<400> SEQUENCE: 8

Ala Asp Lys His Tyr Ala Ile Met Asp Asn Asp Trp Tyr Thr Ala
1               5                   10                  15

<210> SEQ ID NO 9
<211> LENGTH: 9
<212> TYPE: PRT
<213> ORGANISM: Penicillium multicolor

<400> SEQUENCE: 9

Val Glu Thr Lys Leu Ile Phe Leu Thr
1               5

<210> SEQ ID NO 10
<211> LENGTH: 20
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (3)..(3)
<223> OTHER INFORMATION: inosine
<220> FEATURE:
<221> NAME/KEY: misc_feature
<222> LOCATION: (6)..(6)
<223> OTHER INFORMATION: g or a
<220> FEATURE:
<221> NAME/KEY: misc_feature
<222> LOCATION: (9)..(9)
<223> OTHER INFORMATION: t or c
<220> FEATURE:
<221> NAME/KEY: misc_feature
<222> LOCATION: (10)..(10)
<223> OTHER INFORMATION: a or c
<220> FEATURE:
<221> NAME/KEY: misc_feature
<222> LOCATION: (12)..(12)
<223> OTHER INFORMATION: any of a, g, c, or t
<220> FEATURE:
<221> NAME/KEY: misc_feature
<222> LOCATION: (15)..(15)
<223> OTHER INFORMATION: t or c
<220> FEATURE:
<221> NAME/KEY: misc_feature
```

<222> LOCATION: (16)..(16)
<223> OTHER INFORMATION: t or c
<220> FEATURE:
<221> NAME/KEY: misc_feature
<222> LOCATION: (18)..(18)
<223> OTHER INFORMATION: inosine

<400> SEQUENCE: 10
acnaartaym gnttyytnac                                          20

<210> SEQ ID NO 11
<211> LENGTH: 21
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (4)..(4)
<223> OTHER INFORMATION: any of a, g, c, or t
<220> FEATURE:
<221> NAME/KEY: misc_feature
<222> LOCATION: (7)..(7)
<223> OTHER INFORMATION: any of a, g, c, or t
<220> FEATURE:
<221> NAME/KEY: misc_feature
<222> LOCATION: (9)..(9)
<223> OTHER INFORMATION: g or t
<220> FEATURE:
<221> NAME/KEY: misc_feature
<222> LOCATION: (10)..(10)
<223> OTHER INFORMATION: any of a, g, c, or t
<220> FEATURE:
<221> NAME/KEY: misc_feature
<222> LOCATION: (16)..(16)
<223> OTHER INFORMATION: t or c
<220> FEATURE:
<221> NAME/KEY: misc_feature
<222> LOCATION: (19)..(19)
<223> OTHER INFORMATION: any of a, g, c, or t

<400> SEQUENCE: 11
catnccnckn gtccaytgnc c                                        21

<210> SEQ ID NO 12
<211> LENGTH: 26
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (3)..(3)
<223> OTHER INFORMATION: any of a, g, c, or t
<220> FEATURE:
<221> NAME/KEY: misc_feature
<222> LOCATION: (6)..(6)
<223> OTHER INFORMATION: a, c, or t
<220> FEATURE:
<221> NAME/KEY: misc_feature
<222> LOCATION: (12)..(12)
<223> OTHER INFORMATION: t or c
<220> FEATURE:
<221> NAME/KEY: misc_feature
<222> LOCATION: (15)..(15)
<223> OTHER INFORMATION: t or c
<220> FEATURE:
<221> NAME/KEY: misc_feature
<222> LOCATION: (18)..(18)
<223> OTHER INFORMATION: t or c
<220> FEATURE:
<221> NAME/KEY: misc_feature
<222> LOCATION: (24)..(24)
<223> OTHER INFORMATION: t or c

<400> SEQUENCE: 12
gcnathatgg ayaaygaytg gtayac                                    26

<210> SEQ ID NO 13
<211> LENGTH: 23
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (3)..(3)
<223> OTHER INFORMATION: any of a, g, c, or t
<220> FEATURE:
<221> NAME/KEY: misc_feature
<222> LOCATION: (6)..(6)
<223> OTHER INFORMATION: any of a, g, c, or t
<220> FEATURE:
<221> NAME/KEY: misc_feature
<222> LOCATION: (9)..(9)
<223> OTHER INFORMATION: t or c
<220> FEATURE:
<221> NAME/KEY: misc_feature
<222> LOCATION: (12)..(12)
<223> OTHER INFORMATION: g or a
<220> FEATURE:
<221> NAME/KEY: misc_feature
<222> LOCATION: (18)..(18)
<223> OTHER INFORMATION: g or a
<220> FEATURE:
<221> NAME/KEY: misc_feature
<222> LOCATION: (21)..(21)
<223> OTHER INFORMATION: any of a, g, c, or t

<400> SEQUENCE: 13
gcngcngtyt crtcccaraa ngg                                       23

<210> SEQ ID NO 14
<211> LENGTH: 25
<212> TYPE: DNA
<213> ORGANISM: Artificial Sequence
<220> FEATURE:
<223> OTHER INFORMATION: primer

<400> SEQUENCE: 14
atggcaccta agaaaatcat cattg                                     25

<210> SEQ ID NO 15
<211> LENGTH: 25
<212> TYPE: DNA
<213> ORGANISM: Artificial Sequence
<220> FEATURE:
<223> OTHER INFORMATION: primer

<400> SEQUENCE: 15
ttagtggaag attctatcga tgagg                                     25

<210> SEQ ID NO 16
<211> LENGTH: 25
<212> TYPE: DNA
<213> ORGANISM: Artificial Sequence
<220> FEATURE:
<223> OTHER INFORMATION: primer

<400> SEQUENCE: 16
atgcatttcc ctgtttcatt gccgc                                     25

<210> SEQ ID NO 17
<211> LENGTH: 23

```
<212> TYPE: DNA
<213> ORGANISM: Artificial Sequence
<220> FEATURE:
<223> OTHER INFORMATION: primer

<400> SEQUENCE: 17
tcaacgctca tttctcaggt cgg                                               23

<210> SEQ ID NO 18
<211> LENGTH: 574
<212> TYPE: DNA
<213> ORGANISM: Artificial Sequence
<220> FEATURE:
<223> OTHER INFORMATION: probe

<400> SEQUENCE: 18
gaggatcccg aaaccttcct acgtgtcaag gaggtcgttg tgatgggtgg agcaatcaac        60
cagcctggaa atgtatgaac cccgtcgaaa cacccatttg ataataagtc attaaccgcg       120
attgactagg tcacccccgt tggagaattc aacgcctacg cagacgccgt tgcagctgcg       180
cgagtctttg cgctgacatc acctaatccc aactcgactc taccaccgac cacgagtcca       240
ctacttggcc tgtaccctgc aaagctcagc cgacaattga ctctgcgtct cttcccgctg       300
gacatcaccc tgcgccataa cctgtcccgc ggccaattcc gccaagcagt tgagcctctc       360
ctcgcaacag gctcacccct cgctgaatgg gtgacagcat tcatgggaca cacgttccga       420
accctggaac gcctgcaccc cggccatgag ggcgatgaag cccagctgag tctccacgac       480
cctgtctgtg tgtggtatgc ccttacagca gaggattcgc actggactcc ctccgccaat       540
tccccagagg acattcgtgt tgagacattg ggcc                                   574

<210> SEQ ID NO 19
<211> LENGTH: 509
<212> TYPE: DNA
<213> ORGANISM: Artificial Sequence
<220> FEATURE:
<223> OTHER INFORMATION: probe

<400> SEQUENCE: 19
agacaccgca aacacctggc agcctcaggt cgctctgcac gctgtcgcaa ctctggaagc        60
tggcaacttg agctgtatcc ccgtttaccc aggctcgaca tggccgctca tcaacacccc       120
caaccgcttc caggcgtggg aaatggttca tggcaagctg ccatgggagg gtgcttttgc       180
gccggagaac aagactctcg aggccgaggg taacgatcct acctctggca accccaaccg       240
tatcgtcaag gccgctttca aggaagggtt ccccaagggc aagcccgaga acagaacatc       300
tgctgccaac ttcatggtcg agatggtgca caagtacccc ggccaggtct cgatctactc       360
tgctggagcc ctgaccaatg ttgcgctggc tgtgcgcatg gatccccagt ttgcatctct       420
ggctaaggag ttggttatca tgggtggata cgtcgatttg aatatgctcc aggccactgg       480
aagtgtcttg ctggctgatc ttcaatctg                                         509
```

NUCLEOSIDASE

TECHNICAL FIELD

The present invention relates to a novel nucleosidase. More particularly, the invention relates to a nucleosidase useful for reducing purine bodies in foods or beverages. The present application claims priority based on Japanese Patent Application No. 2016-160899 filed on Aug. 18, 2016, the entire contents of which are incorporated herein by reference.

BACKGROUND ART

Prevalence of hyperuricemia and gout based thereon has been on the rise due to westernization of dietary habits and increase in alcohol intake. As a cause of these diseases, purine bodies in foods or beverages have been regarded as a problem. For example, liver, milt or fish eggs, and part of fish and shellfish contain a large amount of purine bodies. Alcoholic beverages, especially brewed alcohols (beer, wine, etc.) also contain a relatively large amount of purine bodies. Alcoholic beverages are often consumed daily, and thus are considered important as risk factors for hyperuricemia and gout. For example, beer-based beverages such as beer and low-malt beer generally contain about 3 to 8 mg of purine bodies derived from raw materials (for example, malt) per 100 mL, and beer/beer-based beverages having a reduced purine body content (low-purine beer/beer-based beverages) are desired.

Attempts to reduce purine bodies in beer have been made so far. For example, in the method described in PTL 1, in the production process, an enzyme (purine nucleoside phosphorylase or nucleosidase) is caused to act on wort, thereby decomposing purine nucleoside in the wort into ribose and free purine bases. The free purine bases are assimilated by yeast during fermentation. As a result, the amount of purine bodies (free purine bases, nucleotides, and nucleosides) in beer products is reduced. PTL 2 also reports a nucleosidase useful for reducing purine bodies in beer. In addition, a method for removing purine bodies by using an adsorbent has also been proposed (PTL 3).

CITATION LIST

Patent Literature

[PTL 1] JP 3824326 B
[PTL 2] JP 3824353 B
[PTL 3] JP 2004-113189 A

SUMMARY OF INVENTION

Technical Problem

Although various techniques for removing purine bodies in beer have been reported as described above, there is no example in which such a technique has been put into practice, and the need for techniques for producing low-purine beer is still high. With regard to beer-based beverages including low-malt beer, it is possible to reduce the purine body content by reducing the malt usage rate or by using raw materials other than malt. However, since the raw materials to be used are restricted, this cannot be said to be a fundamental solution. Accordingly, it is an object of the present invention to provide a novel enzyme useful for reducing purine bodies, especially, in beer or beer-based beverages. It is also an object to provide various uses of the enzyme.

Solution to Problem

Under the above-mentioned problems, the present inventors have screened a wide variety of microorganisms to find an enzyme useful for producing low-purine beer. As a result of studying more than 10,000 kinds of microorganisms, 4 strains of microorganisms have been identified as promising candidates. Assuming that the nucleosidases produced by these microorganisms are used in the beer preparation (mashing) process, the present inventors have evaluated the nucleosidases in terms of the action and effect under general conditions for the preparation process. As a result, it has been revealed that the nucleosidases produced by the three strains are possibly inhibited by the decomposition products (adenine, guanine, hypoxanthine, and xanthine) and cannot exert the desired effect. On the other hand, the nucleosidase produced by the remaining one strain (*Penicillium multicolor* IFO 7569 strain) has not been inhibited by the products and showed high decomposition activity. Therefore, the inventors have decided to attempt to acquire nucleosidases from the bacterial strain. As a result, the inventors have succeeded in purifying two kinds of highly-practicable nucleosidases showing activity even in the presence of adenosine, adenine, inosine, hypoxanthine, guanosine, guanine, and xanthine without undergoing product inhibition. By further studies, the inventors have succeeded in identifying the amino acid sequences of the two kinds of nucleosidases and the genes encoding them, and also succeeded in identifying the properties of each of the nucleosidases. It has become clear that these enzymes are suitable for use in the beer preparation process, especially in terms of the optimum temperature and thermal stability. It has also been revealed that these enzymes show stable activity over a wide pH range and a wide temperature range and are applicable to those other than beer/beer-based beverages (for example, fermented foods such as yogurt and pickles).

As described above, after intensive studies, the inventors have succeeded in acquiring a novel nucleosidase extremely useful for reducing purine bodies in beverages and foods. Based on this result, the following inventions are provided.

[1] A nucleosidase comprising an amino acid sequence of SEQ ID NO: 1 or an amino acid sequence having 85% or more identity with the amino acid sequence, or an amino acid sequence of SEQ ID NO: 2 or an amino acid sequence having 88% or more identity with the amino acid sequence.

[2] The nucleosidase according to [1], wherein the amino acid sequence is an amino acid sequence having 90% or more identity with the amino acid sequence of SEQ ID NO: 1 or the amino acid sequence of SEQ ID NO: 2.

[3] A nucleosidase having the following enzymological properties:

(1) action: catalyzing a reaction of hydrolyzing purine nucleosides into D-ribose and purine bases and showing activity even in the presence of adenosine, adenine, inosine, hypoxanthine, guanosine, guanine, and xanthine;

(2) molecular weight: about 49 kDa (by SDS-PAGE) when the nucleosidase does not contain N-linked oligosaccharides;

(3) optimum temperature: 55° C. to 60° C.; and (4) thermal stability: stable at 55° C. or lower (pH 6.0, for 30 minutes).

[4] The nucleosidase according to [3], further having the following enzymological properties:
(5) optimum pH: 3.5; and
(6) pH stability: stable in the range of pH 3.5 to 7.5 (30° C., for 30 minutes).

[5] A nucleosidase having the following enzymological properties:
(1) action: catalyzing a reaction of hydrolyzing purine nucleosides into D-ribose and purine bases and showing activity even in the presence of adenosine, adenine, inosine, hypoxanthine, guanosine, guanine, and xanthine;
(2) molecular weight: about 40 kDa (by SDS-PAGE) when the nucleosidase does not contain N-linked oligosaccharides;
(3) optimum temperature: 50° C. to 55° C.; and
(4) thermal stability: stable at 65° C. or lower (pH 4.5, for 60 minutes).

[6] The nucleosidase according to [5], further having the following enzymological properties:
(5) optimum pH: 4.5; and
(6) pH stability: stable in the range of pH 3.5 to 7.5 (30° C., for 30 minutes).

[7] The nucleosidase according to any one of [1] to [6], which is derived from *Penicillium multicolor*.

[8] The nucleosidase according to [7], wherein the *Penicillium multicolor* is an IFO 7569 strain or a mutant strain thereof.

[9] A nucleosidase preparation comprising the nucleosidase according to any one of [1] to [8] or a culture solution of a producer microorganism for the nucleosidase according to any one of [1] to [8] or a purified product thereof.

[10] A nucleosidase gene comprising any DNA selected from the group consisting of the following (a) to (c):
(a) a DNA encoding an amino acid sequence of SEQ ID NO: 1 or 2;
(b) a DNA consisting of a base sequence of any of SEQ ID NOs: 3 to 6; and
(c) a DNA having a base sequence equivalent to the base sequence of any of SEQ ID NOs: 3 to 6 and encoding a protein having nucleosidase activity.

[11] A recombinant DNA comprising the nucleosidase gene according to [10].

[12] A microorganism possessing the recombinant DNA according to [11].

[13] A method for producing a nucleosidase, comprising the following steps (1) and (2):
(1) culturing a producer microorganism for the nucleosidase according to any one of [1] to [8]; and
(2) collecting the nucleosidase from the culture solution and/or the cell bodies after culture.

[14] The production method according to [13], wherein the microorganism is a *Penicillium multicolor* IFO 7569 strain or a mutant strain thereof.

[15] A method for producing a nucleosidase, comprising the following steps (i) and (ii):
(i) culturing the microorganism according to [12] under conditions where a protein encoded by the gene is produced; and
(ii) collecting the produced protein.

[16] A method for producing a nucleosidase preparation, comprising the following steps (I) and (II):
(I) culturing a producer microorganism for the nucleosidase according to any one of [1] to [8]; and
(II) removing the cell bodies after culture.

[17] The production method according to [16], further comprising the following step of
(III) purifying the culture solution after removing the cell bodies.

[18] The production method according to [16] or [17], wherein the microorganism is a *Penicillium multicolor* IFO 7569 strain or a mutant strain thereof.

BRIEF DESCRIPTION OF DRAWINGS

FIG. 7 Molecular weight of each purified enzyme (peaks 1 to 3). This figure also shows the results of N-terminal amino acid analysis.

FIG. 8 Probe sequences used for gene cloning. Upper: probe sequence for PN1 (SEQ ID NO: 18) and Lower: probe sequence for PN2 (SEQ ID NO: 19).

FIG. 9 Results of gene cloning. This figure shows a genomic sequence (upper, SEQ ID NO: 4) encoding the enzyme (PN1) of peak 3 and a genomic sequence (lower, SEQ ID NO: 6) encoding the enzyme (PN2) of peaks 1 and 2.

FIG. 10 Results of gene cloning. This figure shows a cDNA sequence (upper, SEQ ID NO: 3) encoding the enzyme (PN1) of peak 3 and a cDNA sequence (lower, SEQ ID NO: 5) encoding the enzyme (PN2) of peaks 1 and 2.

FIG. 11 Results of gene cloning. This figure shows the amino acid sequence of the enzyme (PN1) of peak 3 (upper, SEQ ID NO: 1) and the amino acid sequence of enzyme (PN2) of peaks 1 and 2 (lower, SEQ ID NO: 2).

FIG. 12 Results of gene cloning. The enzyme (PN1) of peak 3 and enzyme (PN2) of peaks 1 and 2 were compared in terms of the number of cDNA bases, number of introns, amino acid length, molecular weight, and estimated pI.

1. Terminology

Figure 1:
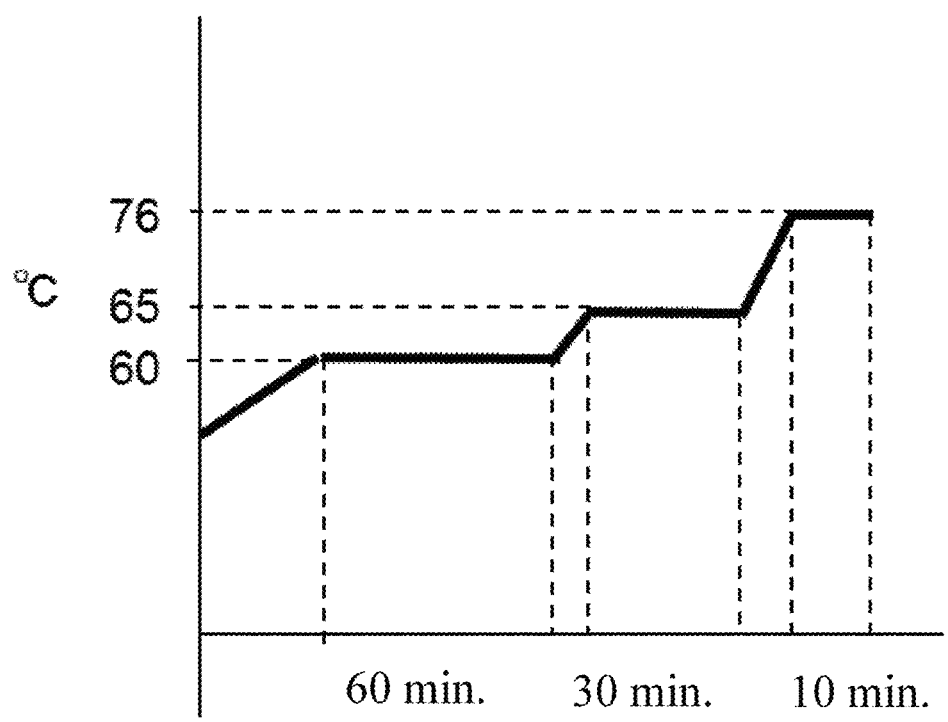
FIG. 1 Reaction process of a mashing (preparation) test.

The term "isolated" as used herein is used exchangeably with "purified." The term "isolated" is used to distinguish a material in a natural state, i.e., in a state in which it occurs in nature, from the material in a state in which it does not occur in nature. By a man-made operation of isolating a material of interest, the material will be in an "isolated state," which is a state different from its natural state. A material that has been isolated is clearly and determinately different from the material itself found in nature.

The purity of an isolated enzyme is not particularly limited. However, if an isolated enzyme is intended to be used for applications requiring that the enzyme be of high purity, then it is preferable that the isolated enzyme have a higher purity.

[Description of Embodiments]

2. Nucleosidase and Producer Bacterium for the Nucleosidase

A first aspect of the present invention provides a nucleosidase and a producer bacterium for the nucleosidase. The present inventors have succeeded in acquiring two kinds of nucleosidases (hereinafter referred to as "PN1" and "PN2" corresponding to the indications in the Examples; in addition, these two nucleosidases are collectively referred to also as "the present enzyme") useful for reducing purine bodies in foods and beverages from *Penicillium multicolor*, and identified the gene sequences and amino acid sequences thereof. Based on the results, the present enzyme has a characteristic feature of including an amino acid sequence of SEQ ID NO: 1 or an amino acid sequence of SEQ ID NO: 2, or an amino acid sequence equivalent to either one of these amino acid sequences. The amino acid sequence of SEQ ID NO: 1 corresponds to PN1, and the amino acid sequence of SEQ ID NO: 2 corresponds to PN2.

The term "equivalent amino acid sequence" in this case means an amino acid sequence which is partially different from the reference amino acid sequence (i.e. the amino acid sequence of SEQ ID NO:1 or the amino acid sequence of SEQ ID NO:2), but the difference does not substantially influence the function of the protein (nucleosidase activity). Thus, an enzyme having a polypeptide chain of the equivalent amino acid sequence shows a nucleosidase activity. The degree of the activity is not particularly limited as long as the function of a nucleosidase can be exhibited, but is preferably equivalent to or higher than that of the enzyme having a polypeptide chain of the reference sequence.

The term "partial difference in the amino acid sequence" typically means mutation (change) in the amino acid sequence caused by deletion or substitution of one to several (up to, for example, 3, 5, 7, or 10) amino acids composing the amino acid sequence, or addition, insertion, or combination thereof of one to several (up to, for example, 3, 5, 7, or 10) amino acids. The difference in the amino acid sequence is acceptable as long as the nucleosidase activity is maintained (the activity may be varied to a degree). As long as the conditions are satisfied, the position of the difference in the amino acid sequence is not particularly limited, and the difference may arise in a plurality of positions. As to the amino acid sequence of SEQ ID NO:1, the term "plurality" means, for example, a number corresponding to less than about 15%, preferably less than about 10%, more preferably less than about 5%, even more preferably less than about 3% of the total amino acids, and most preferably less than about 1%. As to the amino acid sequence of SEQ ID NO:2, the term "plurality" means, for example, a number corresponding to less than about 12%, preferably less than about 10%, more preferably less than about 5%, even more preferably less than about 3% of the total amino acids, and most preferably less than about 1%. More specifically, in a case where the amino acid sequence of SEQ ID NO:1 is the reference amino acid sequence, the equivalent protein has, for example, about 85% or more, preferably about 90% or more, more preferably about 95% or more, much more preferably about 98% or more, and most preferably about 99% or more identity with the reference amino acid sequence, whereas in a case where the amino acid sequence of SEQ ID NO:2 is the reference amino acid sequence, the equivalent protein has, for example, about 88% or more, preferably about 90% or more, more preferably about 95% or more, much more preferably about 98% or more, and most preferably about 99% or more identity with the reference amino acid sequence. The difference of the amino acid sequence may arise in a plurality of positions.

Preferably, the equivalence protein is obtained by causing conservative amino acid substitution in an amino acid residue which is not essential for nucleosidase activity. The term "conservative amino acid substitution" means the substitution of an amino acid residue with another amino acid residue having a side chain with similar properties. Amino acid residues are classified into several families according to their side chains, such as basic side chains (for example, lysine, arginine, and histidine), acidic side chains (for example, aspartic acid and glutamic acid), uncharged polar side chains (for example, glycine, asparagine, glutamine, serine, threonine, tyrosine, and cysteine), nonpolar side chains (for example, alanine, valine, leucine, isoleucine, proline, phenylalanine, methionine, and tryptophan), β branched side chains (for example, threonine, valine, and isoleucine), and aromatic side chains (for example, tyrosine, phenylalanine, tryptophan, and histidine). Conservative amino acid substitution is preferably the substitution between amino acid residues in one family.

The identity (%) between two amino acid sequences or two nucleic acid sequences (hereinafter, the term "two sequences" are used for representing either of two sequences) can be determined by the following procedure. Firstly, two sequences are aligned for optimum comparison of the two sequences (for example, a gap may be introduced into the first sequence so as to optimize the alignment with respect to the second sequence). When a molecule (amino acid residue or nucleotide) at a specific position in the first sequence and a molecule in the corresponding position in the second sequence are the same as each other, the molecules in the positions are defined as being identical. The identity between two sequences is a function of the number of identical positions shared by the two sequences (i.e., identity (%)=number of identical positions/total number of positions×100). Preferably, the number and size of the gaps, which are required to optimize the alignment of the two sequences, are taken into consideration.

The comparison and determination of the identity between two sequences can be carried out by using a mathematical algorithm. A specific example of the mathematical algorithm that can be used for comparing the sequences includes an algorithm described in Karlin and Altschul (1990) Proc. Natl. Acad. Sci. USA 87:2264-68 and modified by Karlin and Altschul (1993) Proc. Natl. Acad. Sci. USA 90:5873-77. However, the algorithm is not necessarily limited to this. Such an algorithm is incorporated in NBLAST program and XBLAST program (version 2.0) described in Altschul et al. (1990) J. Mol. Biol. 215: 403-10. In order to obtain an equivalent nucleic acid sequence, for example, BLAST nucleotide search with score=100 and word length=12 may be carried out by the NBLAST program. In order to obtain an equivalent amino acid sequence, for example, BLAST polypeptide search with score=50 and word length=3 may be carried out by the XBLAST program. In order to obtain gapped alignments for comparison, Gapped BLAST described in Altschul et al., (1997) Amino Acids Research 25(17): 3389-3402 can be utilized. In using BLAST and Gapped BLAST, the default parameters of the corresponding programs (e.g., XBLAST and NBLAST) can be used. In detail, see http://www.ncbi.nlm.nih.gov. Another example of the mathematical algorithm that can be used for comparing sequences includes an algorithm described in Meyers and Miller (1988) Comput. Appl. Biosci. 4: 11-17. Such programs are incorporated into the ALIGN program that can be used for, for example, GENESTREAM network server (IGH Montpellier, France) or ISREC server. When the ALIGN program is used for comparison of the amino acid sequences, for example, PAM120 weight residue table can be used in which a gap length penalty is 12 and a gap penalty is 4.

The identity between two amino acid sequences can be determined by using the GAP program in the GCG software package, using Blossom 62 matrix or PAM250 matrix with the gap weight of 12, 10, 8, 6, or 4, and the gap length weight of 2, 3, or 4. The identity between two nucleic acid sequences can be determined by using the GAP program in the GCG software package (available at http://www.gcg-.com), with the gap weight of 50, and the gap length weight of 3.

The present enzyme may be a portion of a larger protein (for example, a fused protein). Examples of the sequence added to a fused protein include the sequences useful for purification of multiple histidine residues, and addition sequences which ensures stability in recombination production.

The present enzyme having the above-described amino acid sequence is readily prepared by a genetic engineering technique. For example, an appropriate host cell (for example, *Escherichia coli*) is transformed by a DNA encoding the present enzyme, and the protein expressed in the transformant is collected, and thereby preparing the present enzyme. The collected protein is treated as appropriate according to the intended use. The present enzyme thus obtained as a recombinant protein may be subjected to various modifications. For example, the present enzyme composed of a recombinant protein linked to any peptide or protein can be obtained by producing a recombinant protein using a vector into which a DNA encoding the present enzyme has been inserted together with other appropriate DNA. In addition, modification for causing addition of a sugar chain and/or a lipid, or N- or C-terminal processing may be carried out. These modifications allow, for example, extraction of a recombinant protein, simplification of purification, or addition of biological functions.

The present inventors have revealed the enzymological properties of the novel nucleosidases PN1 and PN2 which were successfully acquired. Therefore, the present enzymes PN1 and PN2 can also be characterized by the following enzymological properties.

<Enzymological Properties of PN1>

(1) Action

PN1 is a nucleosidase and catalyzes a reaction of hydrolyzing purine nucleosides into D-ribose and purine bases. The purine nucleoside is a glycoside in which a purine base and a reducing group of sugar are bound by an N-glycoside bond. Examples of the purine nucleoside include adenosine, guanosine, and inosine. In addition, the purine base is a generic term for bases having a purine skeleton, and specific examples thereof include adenine, guanine, hypoxanthine, and xanthine. In addition to purine nucleosides and purine bases, compounds having a purine skeleton including purine nucleotides and the like are collectively referred to as purine bodies.

PN1 shows activity even in the presence of adenosine, adenine, inosine, hypoxanthine, guanosine, guanine, and xanthine. In other words, PN1 is not subject to substantial inhibition by decomposition products. This characteristic feature is particularly important in applying the present enzymes to the production of foods and beverages. According to PN1 exhibiting this characteristic feature, it is possible to efficiently decompose the purine nucleosides derived from the raw materials in the production process of foods and beverages.

(2) Molecular Weight

PN1 contains a sugar chain (i.e., PN1 is a glycoprotein) in its natural form, and the molecular weight before removal of N-linked oligosaccharides was about 53 kDa (molecular weight measured by SDS-PAGE). The molecular weight is about 126 kDa when measured by gel filtration chromatography, and PN1 is presumed to form a dimer. On the other hand, the molecular weight, when measured by SDS-PAGE after removal of N-linked oligosaccharides, was about 49 kDa. Therefore, the molecular weight of the present enzyme when not containing N-linked oligosaccharides is about 49 kDa (molecular weight measured by SDS-PAGE).

(3) Optimum Temperature

The optimum temperature of PN1 is 55° C. to 60° C. This high optimum temperature as described above is advantageous in the application of PN1 to the production of foods and beverages through a treatment process at a relatively high temperature. The optimum temperature can be evaluated by using an acetate buffer (pH 4.3) and also using guanosine as a substrate for quantitating the reaction product ribose.

(4) Thermal Stability

When treated in an acetate buffer (pH 4.5) for 60 minutes, PN1 maintains 80% or more activity under temperature conditions of 45° C. or lower. Therefore, for example, when the temperature during treatment is in the range of 5° C. to 45° C., the residual activity after the treatment becomes 80% or more.

On the other hand, when PN1 is treated in a phosphate buffer (pH 6.0) for 30 minutes, PN1 maintains 80% or more activity under the temperature conditions of 55° C. or lower. Therefore, for example, when the temperature during treatment is in the range of 5° C. to 55° C., the residual activity after the treatment becomes 80% or more.

PN1 which exhibits such excellent thermal stability can show high activity even under relatively high temperature conditions, for example, in the beer preparation process.

PN1 can be further characterized by the following enzymological properties (5) and (6).

(5) Optimum pH

The optimum pH of PN1 is 3.5. The optimum pH is determined based on the measurement results, for example, in a citrate buffer for the pH range of 2.5 to 3.5, in an acetate buffer for the pH range of 3.5 to 5.5, and in a potassium phosphate buffer for the pH range of 5.5 to 6.5.

(6) pH Stability

PN1 shows stable activity in a wide pH range. For example, if the pH of the enzyme solution to be treated is within the range of 3.5 to 7.5, PN1 shows 80% or more of the maximum activity after treatment at 30° C. for 30 minutes. Also, in the case of the treatment at 50° C. for 60 minutes, if the pH of the enzyme solution to be treated is within the range of 3.5 to 7.5, PN1 shows 80% or more of the maximum activity after the treatment. The pH stability is determined based on the measurement results, for example, in a citrate buffer for the pH range of 2.5 to 3.5, in an acetate buffer for the pH range of 3.5 to 5.5, and in a potassium phosphate buffer for the pH range of 5.5 to 6.5.

<Enzymological Properties of PN2>

(1) Action

PN2 is a nucleosidase and catalyzes a reaction of hydrolyzing purine nucleosides into D-ribose and purine bases.

PN2 also shows activity in the presence of adenosine, adenine, inosine, hypoxanthine, guanosine, guanine, and xanthine. In other words, PN2 is not subject to substantial inhibition by decomposition products. This characteristic feature is particularly important in applying the present enzymes to the production of foods and beverages. According to PN2 exhibiting this characteristic feature, it is possible to efficiently decompose the purine nucleosides derived from the raw materials in the production process of foods and beverages.

(2) Molecular Weight

PN2 contains a sugar chain (i.e., PN2 is a glycoprotein) in its natural form, and the molecular weight before removal of N-linked oligosaccharides was about 51 kDa (molecular weight measured by SDS-PAGE). The molecular weight was about 230 kDa when measured by gel filtration chromatography. On the other hand, the molecular weight, when measured by SDS-PAGE after removal of N-linked oligosaccharides, was about 40 kDa. Therefore, the molecular weight of the present enzyme when not containing N-linked oligosaccharides is about 40 kDa (molecular weight measured by SDS-PAGE).

(3) Optimum Temperature

The optimum temperature of PN2 is 50° C. to 55° C. This high optimum temperature as described above is advantageous in the application of PN2 to the production of foods and beverages through a treatment process at a relatively high temperature. The optimum temperature can be evaluated by using an acetate buffer (pH 4.3) and also using guanosine as a substrate for quantitating the reaction product ribose.

(4) Thermal Stability

When treated in an acetate buffer (pH 4.5) for 60 minutes, PN2 maintains 80% or more activity under temperature conditions of 65° C. or lower. Therefore, for example, when the temperature during treatment is in the range of 5° C. to 65° C., the residual activity after the treatment becomes 80% or more.

On the other hand, when treated in a phosphate buffer (pH 6.0) for 30 minutes, PN2 maintains 80% or more activity under the temperature conditions of 55° C. or lower. Therefore, for example, when the temperature during treatment is in the range of 5° C. to 55° C., the residual activity after the treatment becomes 80% or more.

PN2 which exhibits such excellent thermal stability can show high activity even under relatively high temperature conditions, for example, in the beer preparation process.

PN2 can be further characterized by the following enzymological properties (5) and (6).

(5) Optimum pH

The optimum pH of PN2 is 4.5. The optimum pH is determined based on the measurement results, for example, in a citrate buffer for the pH range of 2.5 to 3.5, in an acetate buffer for the pH range of 3.5 to 5.5, and in a potassium phosphate buffer for the pH range of 5.5 to 6.5.

(6) pH Stability

PN2 shows stable activity in a wide pH range. For example, if the pH of the enzyme solution to be treated is within the range of 3.5 to 7.5, PN2 shows 80% or more of the maximum activity after treatment at 30° C. for 30 minutes. In addition, in the case of the treatment at 50° C. for 60 minutes, if the pH of the enzyme solution to be treated is within the range of 4.5 to 7.5, PN2 shows 80% or more of the maximum activity, after the treatment. The pH stability is determined based on the measurement results, for example, in a citrate buffer for the pH range of 2.5 to 3.5, in an acetate buffer for the pH range of 3.5 to 5.5, and in a potassium phosphate buffer for the pH range of 5.5 to 6.5.

The present enzyme preferably is nucleosidase derived from *Penicillium multicolor*. Here, by "nucleosidase derived from *Penicillium multicolor*" is meant a nucleosidase enzyme produced by a microorganism (of either a wild-type strain or a mutant strain) which is classified into *Penicillium multicolor*, or a nucleosidase enzyme obtained by genetic engineering procedures using the nucleosidase gene from a microorganism (of either a wild-type strain or a mutant strain) which is classified into *Penicillium multicolor*. Therefore, "nucleosidase derived from *Penicillium multicolor*" encompasses a recombinant enzyme that is produced by a host microorganism into which the nucleosidase gene (or a modified gene thereof) obtained from *Penicillium multicolor* has been introduced.

A strain of *Penicillium multicolor* is from which the present enzyme is derived is referred to as a producer strain for the present enzyme, for the purpose of description.

As shown in Examples described below, the present inventors have succeeded in isolating and purifying nucleosidases having the above properties from a *Penicillium multicolor* IFO 7569 strain. The *Penicillium multicolor* IFO 7569 strain is a bacterial strain (published as NBRC 7569 in the NBRC Culture catalog) stored in the National Institute of Technology and Evaluation (2-5-8 Kazusakamatari, Kisarazu, Chiba), and can be obtained through prescribed procedures.

3. Gene Encoding Nucleosidase, Recombinant DNA, and Transformant

The second aspect of the invention relates to a gene encoding the present enzyme. In one embodiment, the gene of the invention includes a DNA that encodes an amino acid sequence of SEQ ID NO: 1 or 2. Specific examples of the embodiment are the base sequence of SEQ ID NO: 3, which corresponds to the cDNA encoding the amino acid sequence of SEQ ID NO: 1, the base sequence of SEQ ID NO: 4, which corresponds to the genome DNA encoding the amino acid sequence of SEQ ID NO: 1, the base sequence of SEQ ID NO: 5, which corresponds to the cDNA encoding the amino acid sequence of SEQ ID NO: 2, and the base sequence of SEQ ID NO: 6, which corresponds to the genome DNA encoding the amino acid sequence of SEQ ID NO: 2.

The gene encoding the present enzyme is typically used in preparation of the present enzyme. According to a genetic engineering procedure using the gene encoding the present enzyme, the present enzyme in a more homogeneous state can be obtained. Further, the method can be a preferable method also in the case of preparing a large amount of the present enzyme. Note that uses of the gene encoding the present enzyme are not limited to preparation of the present enzyme. For example, the nucleic acid can also be used as a tool for an experiment intended for clarification of action mechanisms of the present enzyme or a tool for designing or preparing a mutant (modified form) of the present enzyme.

The "gene encoding the present enzyme" herein refers to a nucleic acid capable of obtaining the present enzyme when it is expressed, and includes, as a matter of course of a nucleic acid having a base sequence corresponding to the amino acid sequence of the present enzyme, also a nucleic acid obtained by adding a sequence that does not code for an amino acid sequence to such a nucleic acid. Degeneracy of a codon is also considered.

The gene of the present invention can be prepared in an isolated state by using a standard genetic engineering technique, a molecular biological technique, a biochemical technique, a chemical synthesis, a PCR method (e.g. an overlap extension PCR) or a combination thereof, with reference to sequence information disclosed in the present specification or attached sequence list.

In general, when a part of DNA encoding a certain protein is modified, a protein encoded by the modified DNA may sometimes have the equal function to that of a protein encoded by the DNA before modification. That is to say, the modification of the DNA sequence does not have a substantial effect on the function of the encoded protein, so that the function of the encoded protein may be maintained before and after the modification. Thus, as another embodiment, the present invention provides DNA encoding a protein having a base sequence equivalent to the reference base sequence (i.e., any one of SEQ ID NOs: 3 to 6) and having the nucleosidase activity (hereinafter, which is also referred to as "equivalent DNA"). The "equivalent base sequence" herein denotes a base sequence which is partly different from the reference base sequence but in which the function (herein, nucleosidase activity) of the protein encoded by the sequence is not substantially affected by the difference.

A specific example of the equivalent DNA includes DNA that hybridizes to the complementary base sequence of the reference base sequence under stringent conditions. Herein, the "stringent conditions" are referred to as conditions in which a so-called specific hybrid is formed but a nonspecific hybrid is not formed. Such stringent conditions are known to persons skilled in the art. Such stringent conditions can be set with reference to, for example, Molecular Cloning (Third Edition, Cold Spring Harbor Laboratory Press, New York) and Current protocols in molecular biology (edited by Frederick M. Ausubel et al., 1987). An example of the stringent conditions can include a condition in which a hybridization solution (50% formamide, 10×SSC (0.15 M NaCl, 15 mM sodium citrate, pH 7.0), 5×Denhardt solution, 1% SDS, 10% dextran sulfate, 10 µg/ml denatured salmon sperm DNA, and 50 mM phosphate buffer (pH 7.5)) is used and incubated at about 42° C. to about 50° C., thereafter, washed with 0.1×SSC and 0.1% SDS at about 65° C. to about 70° C. Further preferable stringent conditions can include, for example, a condition in which a hybridization solution 50% formamide, 5×SSC (0.15 M NaCl, 15 mM sodium citrate, pH 7.0), 1×Denhardt solution, 1% SDS, 10% dextran sulfate, 10 µg/ml denatured salmon sperm DNA, and 50 mM phosphate buffer (pH 7.5)) is used.

Another specific example of the equivalent DNA can include DNA encoding a protein having a base sequence which includes substitution, deletion, insertion, addition or inversion in one or a plurality of bases (preferably one to several bases) in the reference base sequence, and which has a β-galactosidase activity. The substitution, deletion, or the like, of the base may occur in a plurality of sites. The "plurality" herein denotes, for example, 2 to 40 bases, preferably 2 to 20 bases, and more preferably 2 to 10 bases, although it depends upon the positions or types of the amino acid residue in the three-dimensional structure of the protein encoded by the DNA.

The equivalent DNA shows a 70% or more identity for example, preferably a 80% or more identity, more preferably a 90% or more identity, more and more preferably a 95% or more identity, and most preferably a 99% or more identity with the reference base sequence (i.e., any one of SEQ ID NOs: 3 to 6).

The above-mentioned equivalent DNA can be obtained by modifying the reference DNA so as to include substitution, deletion, insertion, addition and/or inversion of base by using treatment with a restriction enzyme; treatment with exonuclease, DNA ligase, etc; introduction of mutation by a site-directed mutagenesis (Molecular Cloning, Third Edition, Chapter 13, Cold Spring Harbor Laboratory Press, New York) and random mutagenesis (Molecular Cloning, Third Edition, Chapter 13, Cold Spring Harbor Laboratory Press, New York), and the like. Furthermore, the equivalent DNA can be also obtained by other methods such as irradiation with ultraviolet ray. A further example of the equivalent DNA can include DNA having difference in base as mentioned above due to polymorphism represented by SNP (single nucleotide polymorphism).

Another embodiment of the present invention relates to a nucleic acid having the complementary base sequence to the base sequence of the gene encoding the present enzyme. Another embodiment of the present invention provides a nucleic acid having a base sequence with an identity of at least about 60%, 70%, 80%, 90%, 95%, 99%, or 99.9% to the base sequence of the gene encoding the present enzyme or the complementary base sequence thereto.

Another aspect of the present invention relates to a recombinant DNA containing the gene of the present invention (the gene encoding the present enzyme). The recombinant DNA of the invention is provided in, for example, a form of a vector. The term "vector" in the present specification refers to a nucleic acid molecule that can transfer a nucleic acid inserted in the vector to a target such as a cell.

A suitable vector is selected according to its intended use (cloning, expression of a protein) and in consideration of a kind of a host cell. Examples include a M13 phage or an altered form thereof, a λ phage or an altered form thereof, and pBR322 or an altered form thereof (e.g., pB325, pAT153, pUC8), etc. as a vector having *Escherichia coli* as a host, pYepSec1, pMFa, and pYES2 as a vector having a yeast as a host, pAc, pVL, etc. as a vector having an insect cell as a host, and pCDM8, pMT2PC, etc. as a vector having a mammal cell as a host.

The vector of the present invention is preferably an expression vector. The "expression vector" refers to a vector capable of introducing a nucleic acid inserted in the expression vector into a target cell (host cell) and expressing it in the cell. The expression vector generally contains a promoter sequence necessary for expression of a nucleic acid inserted, an enhancer sequence for promoting expression, and the like. An expression vector containing a selective marker can also be used. When such an expression vector is used, presence or absence (and its degree) of introduction of the expression vector can be confirmed using a selective marker.

Insertion of DNA into the vector, insertion of a selective marker gene (if necessary), insertion of a promoter (if necessary), and the like can be performed by using a standard recombinant DNA technique (for example, a known method of using a restriction enzyme and a DNA ligase, which can be referred in Molecular Cloning, Third Edition, 1.84, Cold Spring Harbor Laboratory Press, New York).

The present invention further relates to a transformant into which the recombinant DNA, which contains the gene of the present invention, of the present invention is introduced. In the transformant of the preset invention, the gene of the present invention exists as an exogenous molecule. Preferably, the transformant of the present invention can be preferably prepared by transfection or transformation using the vector of the present invention mentioned above. The transfection and transformation can be carried out by, for example, a calcium phosphate coprecipitation method, electroporation (Potter, H. et al., Proc. Natl. Acad. Sci. U.S.A. 81, 7161-7165(1984)), lipofection (Feigner, P. L. et al., Proc. Natl. Acad. Sci. U.S.A. 84, 7413-7417 (1984)), microinjection (Graessmann, M. & Graessmann, A., Proc. Natl. Acad. Sci. U.S.A. 73, 366-370 (1976)), a method by Hanahan (Hanahan, D., J. Mol. Biol. 166, 557-580 (1983)), a lithium acetate method (Schiestl, R. H. et al., Curr. Genet. 16, 339-346 (1989)), protoplast-polyethylene glycol method (Yelton, M. M. et al., Proc. Natl. Acad. Sci. 81, 1470-1474 (1984)), and the like.

The host cell is not particularly limited as long as the present enzyme can be expressed, and it can be selected from, for example, *Bacillus* genus bacteria (e.g. *Bacillus subtillis, Bacillus licheniformis, Bacillus circulans*, etc.), lactic acid bacteria (e.g. *Lactococcus, Lactobacillus, Streptococcus, Leuconostoc, Bifidobacterium*, etc.), other bacteria (e.g. *Escherichia, Streptomyces*, etc.), yeast (e.g. *Saccharomyces*, Kluyveromyces, Candida, Torula, Torulopsis, etc.), and filamentous fungi (Eumycetes) (e.g. *Aspergillus* genus fungi such as *Aspergillus oryzae* and *Aspergillus niger, Penicillium* genus fungi, *Trichoderma* genus fungi, *Fusarium* genus fungi, etc.).

4. Method for Producing Nucleosidase

A third aspect of the present invention provides a method for producing a nucleosidase. One embodiment of the production method according to the present invention involves the step (step (1)) of culturing a producer microorganism for the present enzyme and the step (step (2)) of collecting the nucleosidase from the culture solution and/or the cell bodies after culture. The producer microorganism for the present enzyme is, for example, *Penicillium multicolor*, preferably a *Penicillium multicolor* IFO 7569 strain or a mutant strain thereof. The mutant strain can be obtained, for example, by irradiation with ultraviolet rays, X rays, γ rays, or the like, or treatment with nitrous acid, hydroxylamine, N-methyl-N'-nitro-N-nitrosoguanidine, or the like.

Conditions and methods for culturing cells are not particularly limited, as long as the inventive enzyme is produced. Thus, methods and culture conditions that are suitable for culturing a microorganism to be used can be set as appropriate, with the proviso that the inventive enzyme is produced. Although the culturing may be by either liquid culture or solid culture, liquid culture is preferably employed. Taking liquid culture as an example, culturing conditions therefor will be described below.

As the medium, any medium can be used as long as microorganisms to be used can grow. For example, a medium supplemented with a carbon source such as glucose, sucrose, gentiobiose, soluble starch, glycerin, dextrin, molasses, and organic acid; and further, a nitrogen source such as ammonium sulfate, ammonium carbonate, ammonium phosphate, ammonium acetate, or peptone, yeast extract, corn steep liquor, casein hydrolysate, bran, and meat extract; and furthermore, an inorganic salt such as potassium salt, magnesium salt, sodium salt, phosphate salt, manganese salt, iron salt, and zinc salt, and the like, can be used. In order to promote the growth of transformants to be used, vitamin, amino acid, and the like, may be added to the medium. The medium is cultured under the aerobic conditions such that the pH of the medium is adjusted to, for example, about 3 to 8 (preferably about 4 to 7), and the culture temperature is generally about 20° C. to 40° C. (preferably about 25° C. to 35° C.) for 1 to 20 days (preferably 3 to 10 days). An example of the culture method may include a shake culture method, and an aerobic submerged culture method by using a jar fermenter.

After culturing under the above conditions, the target protein is collected from the culture solution or the cell bodies (step (2)). When it is collected from the culture solution, the present enzyme can be obtained by separation and purification by removing insoluble matters by, for example, filtration of culture supernatant, centrifugation, and the like, followed by carrying out, for example, concentration by ultrafiltration membrane, salting out by ammonium sulfate precipitation, dialysis, various types of chromatography of an ion-exchange resin or an appropriate combination thereof. On the other hand, when it is collected from cell bodies, the target protein can be obtained by pulverizing the cell bodies by pressuring treatment, ultrasonic treatment, or the like, followed by separation and purification thereof similar to the above. After collection of the cell bodies from a culture solution by filtration, centrifugation, etc., a series of processes (pulverizing, separation, and purification of cell bodies) mentioned above may be carried out.

In another embodiment of the present invention, the nucleosidase is produced by using the above-mentioned transformant. In the production method in this embodiment, the transformant is cultured under the conditions such that a protein encoded by a gene introduced therein is produced (step (i)). The culture conditions of transformant are known as to various vector-host systems, and a person skilled in the art can easily set an appropriate culture condition. Following to the culturing step, the produced protein (nucleosidase) is collected (step (ii)). Collection and following purification can be conducted in the same manner as the above embodiment.

The purification degree of nucleosidase is not particularly limited. Furthermore, the final form of the β-galactosidase may be a liquid state or a solid state (including a powdery state).

The purified enzyme obtained as described above can be provided after being powdered, for example, by freeze dry, vacuum dry, or spray dry. In this time, the purified enzyme may be previously dissolved in a phosphoric acid buffer solution, a triethanol amine buffer solution, a tris-hydrochloric acid buffer solution, or a GOOD buffer solution. Preferably, a phosphoric acid buffer solution and a triethanol amine buffer solution can be used. Note that, for the GOOD buffer solution herein, PIPES, MES or MOPS is exemplified.

5. Enzyme Preparation (Nucleosidase Preparation)

The present enzyme is provided, for example, in the form of an enzyme preparation (nucleosidase preparation). The enzyme preparation may contain an excipient, a buffer agent, a suspending agent, a stabilizer, a preservative, an antiseptic, saline and the like besides the active ingredient (i.e. the present enzyme). The degree of purity of the present enzyme is not particularly limited. Thus, the present enzyme may be a crude or purified enzyme. As the excipient, lactose, sorbitol, D-mannitol, maltodextrin, white soft sugar, common salt and the like can be used. As the buffer agent, phosphates, citrates, acetates and the like can be used. As the stabilizer, propylene glycol, ascorbic acid and the like can be used. As the preservative, phenol, benzalkonium chloride, benzyl alcohol, chlorobutanol, methylparaben and the like can be used. As the antiseptic, benzalkonium chloride, paraoxybenzoic acid, chlorobutanol and the like can be used.

In one embodiment of the present enzyme preparation, in order to obtain a liquid enzyme preparation through simple operations, an enzyme preparation is produced by a production method including the following steps (I) and (II):

(I) culturing a producer microorganism for the present enzyme; and (II) removing the cell bodies after culture.

Step (I) is similar to the above step (1) in the method for producing the present enzyme, and thus the explanation thereof will be omitted. In step (II) following step (I), the cell bodies are removed by centrifugation, filtration, filter treatment, or the like. The thus-obtained culture solution containing no cell body is used as an enzyme preparation as it is or after further treatment (i.e., the step (step (III)) of purifying the culture solution after removing the cell bodies). Examples of the further treatment referred to herein can include concentration with an ultrafiltration membrane.

6. Use of Nucleosidase

A further aspect of the present invention provides use of the present enzyme or the present enzyme preparation. As a first use, a method for producing beer or beer-based beverages is provided. The "beer-based beverages" include "low-malt beer" with a reduced malt usage rate and beer-flavored effervescent alcoholic drinks (commonly referred to as "third beers") made from raw materials and by a process, which raw materials and process are different from those for beer and low-malt beer. The third beers are roughly divided into those brewed without using malt as a raw material and those made by blending a different alcoholic drink (as a representative, barley spirits) in low-malt beers. Under the current Liquor Tax Law, the former is classified under the category "other brewed alcohols (effervescent) (1)", and the latter is classified under the category "liqueur (effervescent) (1)". Hereinafter, a mode of use will be described by taking, as an example, a case where the present enzyme or the present enzyme preparation is applied to the production of beer. Note that this applies also to beer-based beverages.

When the present enzyme or the present enzyme preparation is applied to the production of beer, the present enzyme is caused to act on wort in the beer production process, and the purine nucleosides in the wort are decomposed into D-ribose and purine bases. The yeast used for beer fermentation usually cannot assimilate purine nucleosides, but can assimilate free purine bases. Therefore, if the purine nucleosides in the wort are converted into free purine bases by the action of the present enzyme, yeast assimilates free purine bases during the fermentation process, so that beer with a reduced total content of purine bodies is obtained.

The present enzyme or the present enzyme preparation is useful also for the purpose of reducing purine bodies in foods or beverages other than beer or beer-based beverages. When the present enzyme or the present enzyme preparation is used in the production process of foods or beverages, the purine nucleosides derived from the raw materials can be converted into free purine bases. If the free purine bases are removed in the subsequent production process, foods/beverages with a reduced content of purine bodies can be obtained. Therefore, the present enzyme or the present enzyme preparation can be applied to the production of foods or beverages from which free purine bases can be removed in the production process. Examples of the corresponding foods and beverages include foods and beverages utilizing fermentation by microorganisms that can assimilate free purine bases, i.e., fermented foods and fermented beverages. Specifically, various pickles, miso, soy sauce, yogurt, fermented milk, lactic acid bacteria beverage, shaoxing wine, and wine are exemplified. In the application of the present enzyme/the present enzyme preparation to the production of these foods and beverages, for example, the present enzyme/enzyme preparation is added to raw materials before or during fermentation to act thereon, thereby decomposing the purine nucleosides in the raw materials into D-ribose and purine bases. The produced purine bases are typically assimilated by microorganisms during fermentation. As a result, foods or beverages having a reduced total content of purine bodies can be obtained.

EXAMPLES

1. Acquisition of Novel Nucleosidase

More than 10,000 kinds of microorganisms were screened in order to find an enzyme useful for producing low-purine beer. As a result, four strains of microorganisms, i.e., a *Penicillium multicolor* IFO 7569 strain, a *Bacillus brevis* IFO 15304 strain, a *Brevibacillus linens* IFO 12141 strain, and a *Mucor javanicus* 4068 strain were identified as promising candidates. Assuming that the nucleosidases produced by these microorganisms were used in the beer preparation process, the nucleosidases were evaluated in terms of the action and effect under general conditions (mashing test) for the preparation process.

(1) Method for Culturing *Penicillium multicolor* IFO 7569 Strain

A *Penicillium multicolor* IFO 7569 strain was inoculated into 100 mL of the following culture medium B and cultured with shaking in a Sakaguchi flask with a volume of 500 mL at 27° C. for 48 to 72 hours. This preculture solution was transferred to 2 L of the following culture medium B and cultured with aeration and agitation at 27° C. for 120 to 188 hours. This culture solution was filtered through diatomaceous earth to remove cell bodies. The culture supernatant obtained after removal of the cell bodies was concentrated with an ultrafiltration membrane to obtain lyophilized powders.

<Culture Medium A>

1% Lustergen FK (Nippon Starch Chemical Co., Ltd.)
1% Yeast extract (Difco)
0.5% NaCl
pH 7.0

<Culture Medium B>
1% Lustergen FK (Nippon Starch Chemical Co., Ltd.)
1% Yeast extract (Difco)
2% Cornmeal (Matsumoto Nosan K.K.)
0.5% NaCl
pH 6.5

(2) Method for Culturing *Bacillus brevis* IFO 15304 Strain, *Brevibacillus linens* IFO 12141 Strain, and *Mucor javanicus* 4068 Strain A *Bacillus brevis* IFO 15304 strain and a *Brevibacillus linens* IFO 12141 strain were each inoculated into 10 mL of the above culture medium A and cultured with shaking at 30° C. for 48 hours in a test tube. On the other hand, a *Mucor javanicus* IFO 4068 strain was inoculated into the above culture medium B 10 mL and cultured under the same conditions. The culture solutions were each transferred to 50 mL of the main culture medium having the same composition and cultured with shaking at 30° C. for 120 hours. The culture solutions were centrifuged to remove cell bodies to obtain lyophilized powders from the supernatants after removal of the cell bodies.

(3) Measurement of Nucleosidase Activity

The nucleosidase activity was defined by quantitating ribose produced by a reaction using guanosine as a substrate. In 1 mL of a reaction solution, a 0.1M acetate buffer (pH 4.3), 8 mM of guanosine and an appropriate amount of an enzyme are contained. The reaction started with addition of guanosine, and was carried out at 55° C. for 30 minutes. The reaction was stopped by adding 1.5 mL of a 0.5% dinitro salicylic acid solution, and then the solution was boiled for 10 minutes. The absorbance at 540 nm of the reaction solution after cooling was measured, and the activity value was calculated from the value obtained by subtracting the absorbance of an enzyme-free reaction solution. The amount of the enzyme producing 1 µmol of ribose in 30 minutes was defined as 1 U of enzyme activity.

(4) Mashing Test

Together with 80 g of pulverized malt and 320 mL of water, each nucleosidase was added in an amount equivalent to 320 U, and a mashing test was carried out to prepare wort. The reaction process is shown in FIG. 1. The amount of each purine body in the wort after mashing was quantitatively analyzed by high performance liquid chromatography under the following conditions.

Figure 2:
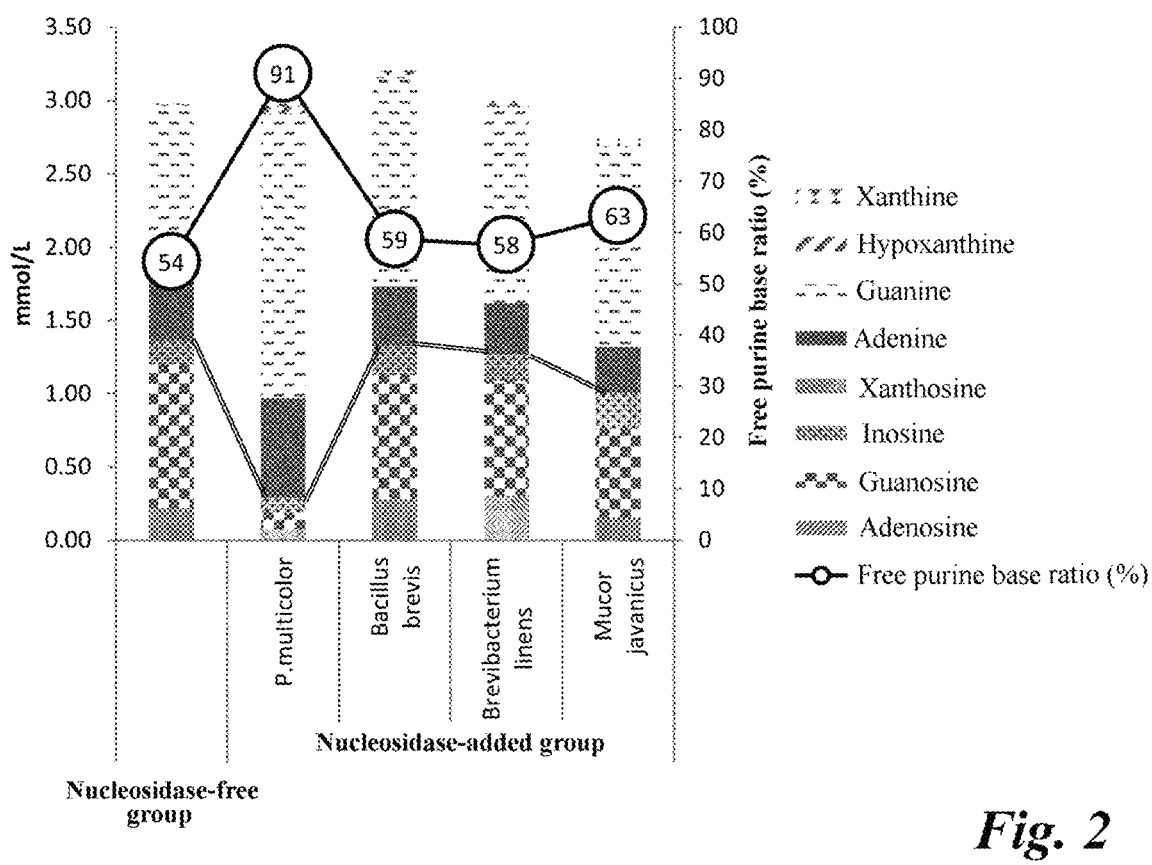
FIG. 2 Comparison in amounts of purine bodies in wort. The amounts of the respective purine bodies in the wort after mashing were analyzed by high performance liquid chromatography.

<HPLC Conditions>
Column: Asahipak GS-220 HQ
Mobile phase: 150 mM sodium phosphate buffer (pH 2.5)
Temperature: 35° C.
Flow rate: 0.5 mL/min
Detection: 260 nm The analysis results are shown in FIG. 2. In the figure, the free purine base ratio is also shown based on the following calculation formula:

Free purine base ratio (%)={purine base/(purine nucleoside+purine base)}×100.

In the wort to which the nucleosidase derived from the *Penicillium multicolor* (*P. multicolor*) IFO 7569 strain was added, the purine nucleosides decreased and the purine bases increased. In contrast, the nucleosidases from the *Bacillus brevis* IFO 15304 strain, the *Brevibacillus linens* IFO 12141 strain, and the *Mucor* javanicus 4068 strain seemed to have been probably inhibited by degradation products (adenine, guanine, hypoxanthine, and xanthine), and there were no significant changes in amounts of the purine nucleosides.

(5) Study on Properties of Nucleosidase Derived From *Penicillium multicolor* IFO 7569 Strain (*P. multicolor* nucleosidase)

In order to investigate the properties of the *P. multicolor* nucleosidase, a solution having the following composition (hereinafter referred to as simulated wort) was used to review the operative temperature range and the operative pH range.

Figure 3:
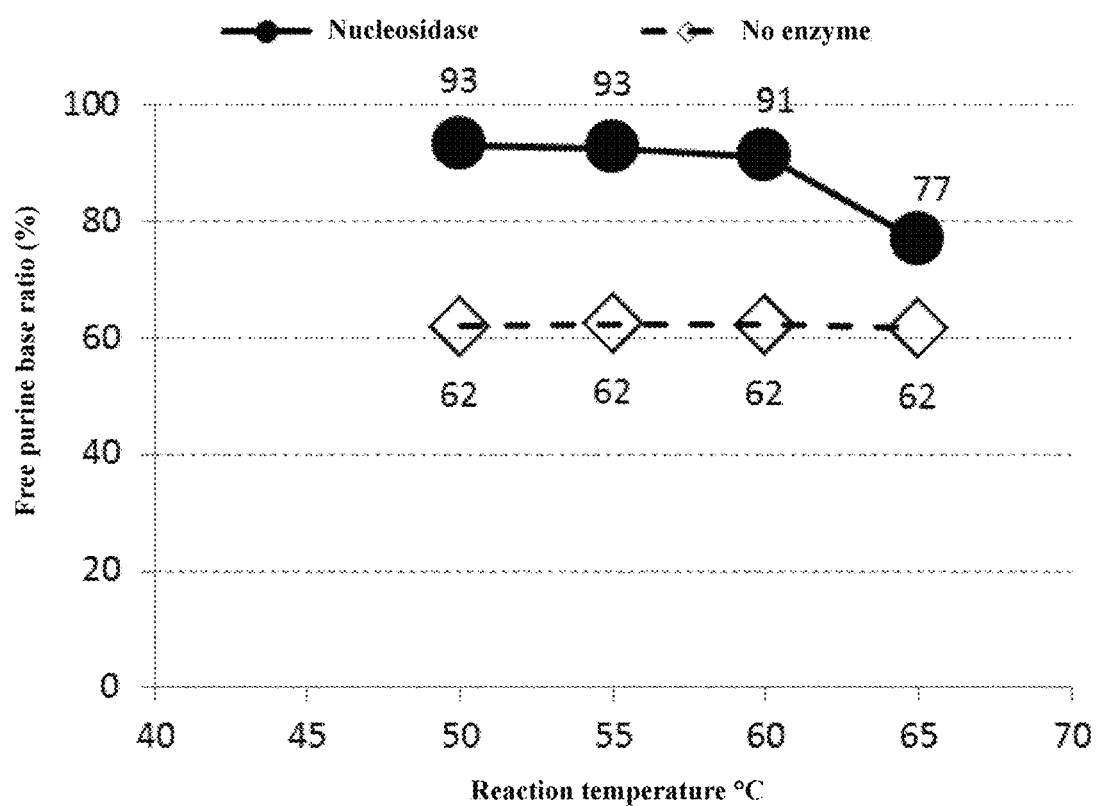
FIG. 3 Operative temperature range of a nucleosidase derived from a *Penicillium multicolor* IFO 7569 strain. An enzymatic reaction was carried out under each temperature condition in the presence of seven kinds of purine bodies, and the free purine base ratio was determined.

Adenosine 0.08 mmol/L
Adenine 0.43 mmol/L
Inosine 0.49 mmol/L
Hypoxanthine 0.08 mmol/L
Guanosine 0.67 mmol/L
Guanine 1.45 mmol/L
Xanthosine 0.00 mmol/L
Xanthine 0.08 mmol/L (5-1) Operative Temperature Range To 2 mL of simulated wort, 9 U of the *P. multicolor* nucleosidase was added to cause a reaction at pH 5.5 for 1 hour at each temperature, then diluted 10 times with a 150 mM sodium phosphate buffer (pH 2.5) as the mobile phase of HPLC, and quantitatively analyzed by high performance liquid chromatography. The free purine base ratio was calculated based on the following calculation formula. At the reaction temperature of 50° C. to 60° C., the free purine base ratio became 90% or more (FIG. 3).

Free purine base ratio (%)={purine base/(purine nucleoside+purine base)}×100.

(5-2) Operative pH Range

Figure 4:
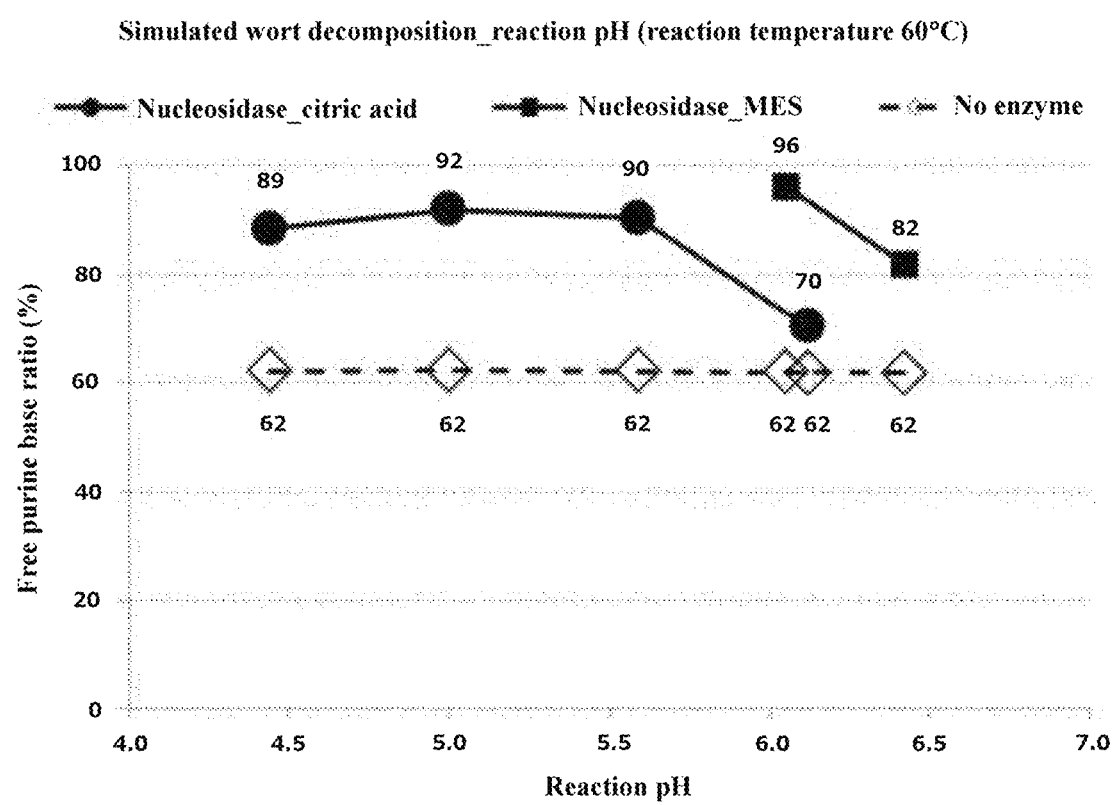
FIG. 4 Operative pH range of the nucleosidase derived from the *Penicillium multicolor* IFO 7569 strain. An enzymatic reaction was carried out under each pH condition in the presence of seven kinds of purine bodies, and the free purine base ratio was determined.

To 2 mL of simulated wort, 9 U of the *P. multicolor* nucleosidase was added to cause a reaction at 55° C. for 1 hour at each pH, then diluted 10 times with a 150 mM sodium phosphate buffer (pH 2.5) as the mobile phase of HPLC, and quantitatively analyzed by high performance liquid chromatography. A citrate buffer was used when the pH was 4.5 to 6.0, and an MES buffer was used when the pH was 6.0 to 6.5. As in the case of the study on the operative temperature range, the free purine base ratio was calculated. In the citrate buffer, the free purine body ratio was 80% or more when the pH was 4.5 to 5.5. In the MES buffer, the free purine body ratio was 80% or more when the pH was 6.0 to 6.5 (FIG. 4).

Figure 5:
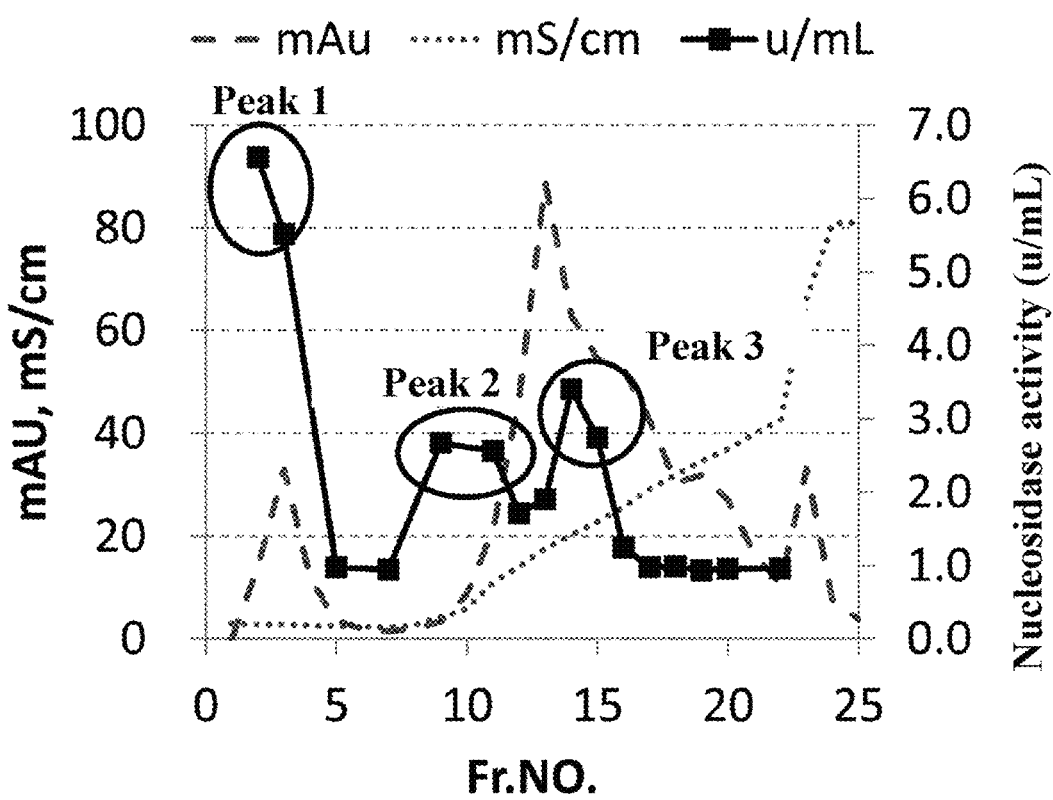
FIG. 5 Purification of the nucleosidase from the *Penicillium multicolor* IFO 7569 strain. This figure shows the results of DEAE HP column chromatography.

(6) Purification of Nucleosidase Derived From *Penicillium multicolor* IFO 7569 Strain The nucleosidase was purified by hydroxyapatite column, anion exchange column, hydrophobic column, and gel filtration column chromatographies. A series of purification processes will be shown below. First, 0.1 g of the lyophilized powder prepared from the culture solution of the *Penicillium multicolor* IFO 7569 strain was dissolved in 5 mL of a buffer (5 mM potassium phosphate buffer (pH 6)+0.3 M NaCl), and the solution was applied to a hydroxyapatite column (Bio-Rad) equilibrated with the same buffer. The adsorbed protein was eluted with a phosphoric acid gradient of 5 mM to 300 mM, and an active fraction was collected. The obtained active fraction was dialyzed against a buffer (20 mM potassium phosphate buffer (pH 5.5)) and applied to a DEAE HP column (GE Healthcare) equilibrated with the same buffer. When the adsorbed protein was eluted with an NaCl gradient of 0 mM to 500 mM, three peaks were observed (FIG. 5). Fr. 2 was defined as peak 1, Fr. 8 and Fr. 9 as peak 2, and Fr. 14 and Fr. 15 as peak 3.

Figure 6:
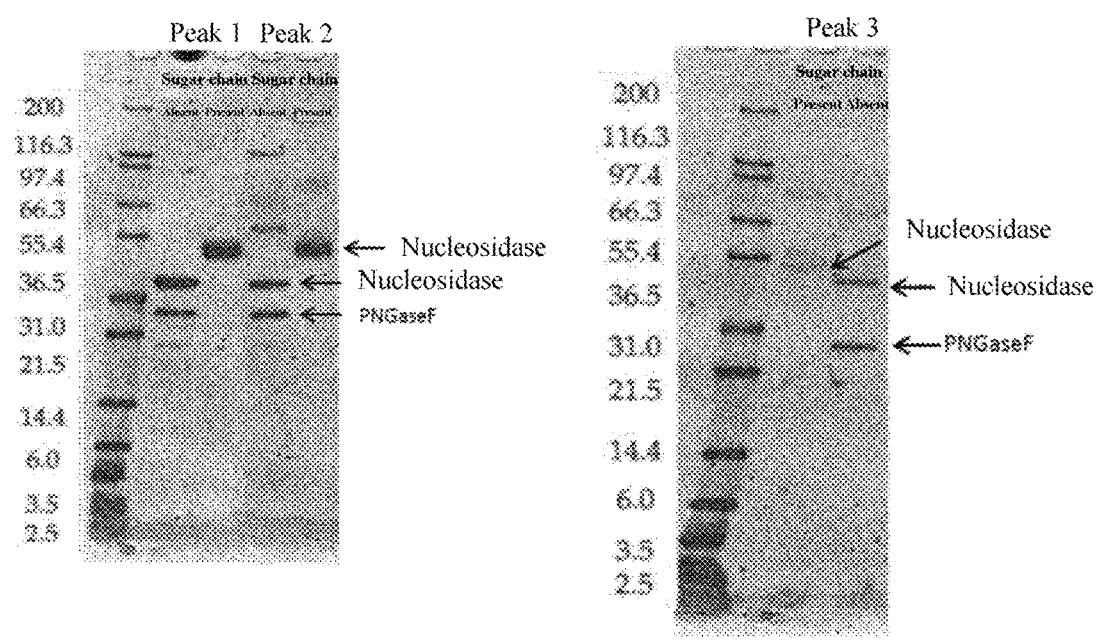
FIG. 6 Measurement results of the molecular weight of each purified enzyme (peaks 1 to 3) (SDS-PAGE). The left shows the results of peaks 1 and 2. The right shows the results of peak 3. A sample after PNGase F treatment ("sugar chain absent" lane) and an untreated sample ("sugar chain present" lane) were electrophoresed and stained with CBB. The leftmost lane shows molecular weight markers (myosin (200 kDa), β-galactosidase (116.3 kDa), phosphorylase B (97.4 kDa), BSA (66.3 kDa), glutamate dehydrogenase (55.4 kDa), lactic acid dehydrogenase (36.5 kDa), carbonate anhydrase (31.0 kDa), trypsin inhibitor (21.5 kDa), lysozyme (14.4 kDa), aprotinin (6.0 kDa), insulin B chain (3.5 kDa), and insulin A chain (2.5 kDa)).

The collected peak 3 was dialyzed against a buffer (20 mM acetate buffer (pH 4.5)+30% saturated ammonium sulfate), and applied to a Phenyl HP column (GE Healthcare) equilibrated with the same buffer. The adsorbed protein was eluted with an ammonium sulfate gradient of 30% saturation to 0%, and the active fraction was collected. The obtained active fraction was dialyzed with a buffer (20 mM sodium phosphate buffer (pH 6)) and then concentrated to 0.5 mL using an ultrafiltration membrane. The concentrated active fraction was applied to HiLoad 16/60 Superdex 200 (GE Healthcare) equilibrated with the same buffer, and an active fraction was collected. The obtained purified enzyme was confirmed to show a single band by SDS-PAGE (FIG. 6). The molecular weight was estimated to be about 53 kDa by SDS-PAGE and about 126 kDa by gel filtration chromatography (FIG. 7). The sugar chains of the resultant purified enzyme were removed with PNGase F (New England BioLabs). The treatment method was in accordance with the attached protocol. By SDS-PAGE after the treatment, it was shown that the molecular weight decreased from about 53 kDa to about 49 kDa by removal of the N-linked oligosaccharides (FIGS. 6 and 7). The collected peaks 1 and 2 were similarly purified, and their molecular weight was determined by SDS-PAGE and gel filtration chromatography. The molecular weight was estimated to be about 51 kDa by SDS-PAGE and about 230 kDa by gel filtration chromatography (FIG. 7). The sugar chains of the resultant purified enzyme were removed with PNGase F (New England BioLabs). By SDS-PAGE after the treatment, it was shown that the molecular weight decreased from about 51 kDa to about 40 kDa by removal of the N-linked oligosaccharides (FIGS. 6 and 7).

When the N-terminal amino acid sequence of the respective purified enzymes (peaks 1 to 3) were analyzed with a protein sequencer (Shimadzu Corporation), the following sequences were estimated.

```
N-terminal amino acid sequence of peak 1:
                                       (SEQ ID NO: 7)
ADKHYAIMDNDWYTA N-terminal amino acid sequence of peak 2:
                                       (SEQ ID NO: 8)
ADKHYAIMDNDWYTA N-terminal amino acid sequence of peak 3:
                                       (SEQ ID NO: 9)
VETKLIFLT
```

Peak 1 and peak 2 had the same molecular weight and N-terminal amino acid sequence, and thus were estimated to be the same enzymes (FIG. 7). In the subsequent study, the enzymes were called PN2, and the enzyme of peak 3 was called PN1.

2. Gene Cloning

The following degenerate primers were designed from the determined N-terminal amino acid sequences and nucleosidase conserved sequences, and PCR was carried out using the P. multicolor genomic DNA as a template.

```
<Degenerate primer for PN1>
FW:
                                      (SEQ ID NO: 10)
ACIAARTAYMGNTTYYTIAC

RV:
                                      (SEQ ID NO: 11)
CATNCCNCKNGTCCAYTGNCC

<Degenerate primer for PN2>
FW:
                                      (SEQ ID NO: 12)
GCNATHATGGAYAAYGAYTGGTAYAC RV:
                                      (SEQ ID NO: 13)
GCNGCNGTYTCRTCCCARAANGG
```

The obtained amplified fragments were subcloned into pMD20-T (TaKaRa) and sequenced. Southern blotting and colony hybridization were carried out using the probes shown in FIG. 8. The obtained fragments were sequenced to identify the base sequences (FIG. 9) in the genomes of PN1 and PN2.

Next, cDNA was prepared from mRNA prepared from the P. multicolor genomic DNA using SMARTER RACE 5'/3' (TaKaRa). Then, PCR was carried out using the following primers, and the amplified fragments were sequenced to determine the base sequences of PN1 and PN2 in the cDNA (FIG. 10). From the determined base sequences, amino acid sequences of PN1 and PN2 were identified (FIG. 11). In FIG. 12, PN1 and PN2 were compared.

```
<PCR primer for PN1>
FW:
                                      (SEQ ID NO: 14)
ATGGCACCTAAGAAAATCATCATTG RV:
                                      (SEQ ID NO: 15)
TTAGTGGAAGATTCTATCGATGAGG <PCR primer for PN2>
FW:
                                      (SEQ ID NO: 16)
ATGCATTTCCCTGTTTCATTGCCGC RV:
                                      (SEQ ID NO: 17)
TCAACGCTCATTTCTCAGGTCGG
```

3. Study on Various Properties of Enzyme PN1

(1) Optimum Temperature

Figure 13:
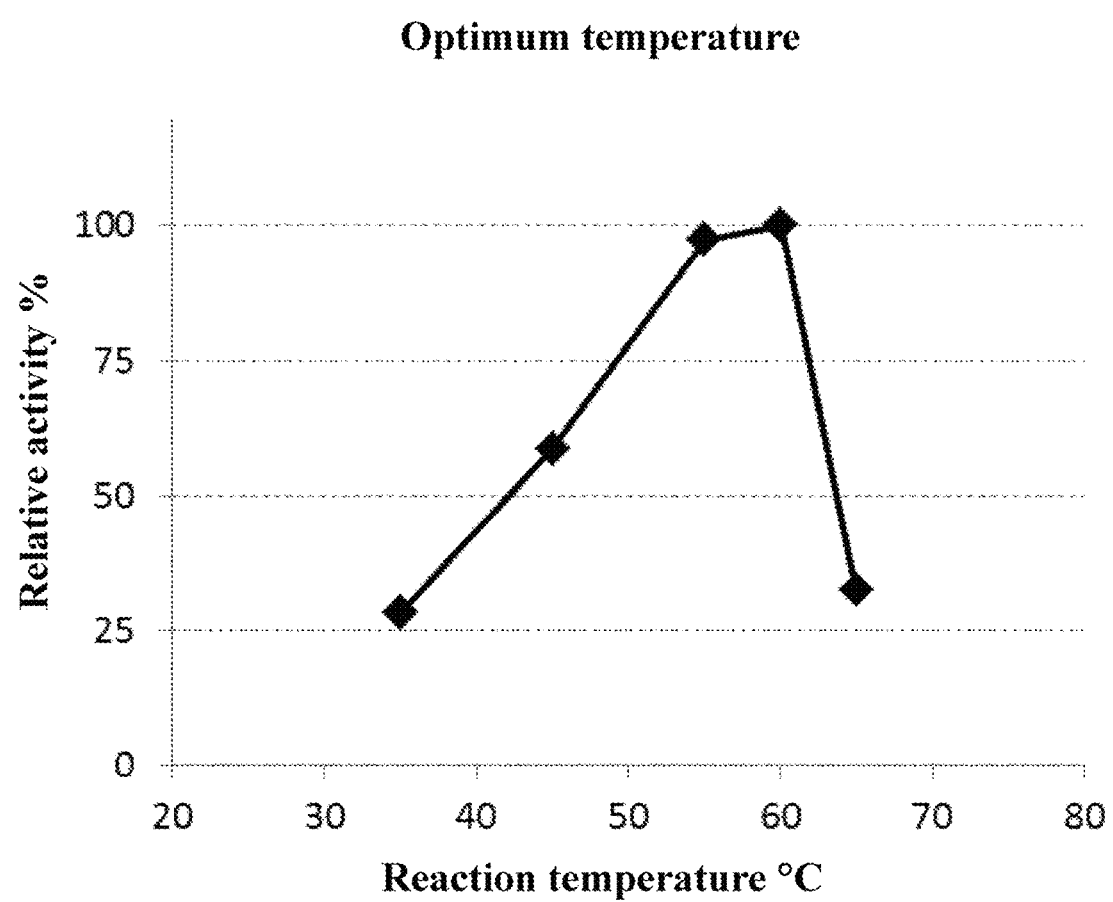
FIG. 13 Optimum temperature of the purified enzyme (PN1).

The optimum temperature of the nucleosidase (PN1) of peak 3 collected from the DEAE HP column was analyzed. The results at the respective temperatures are shown in FIG. 13. The optimum temperature under the conditions was 55° C. to 60° C.

(2) Thermal Stability

Figure 14:
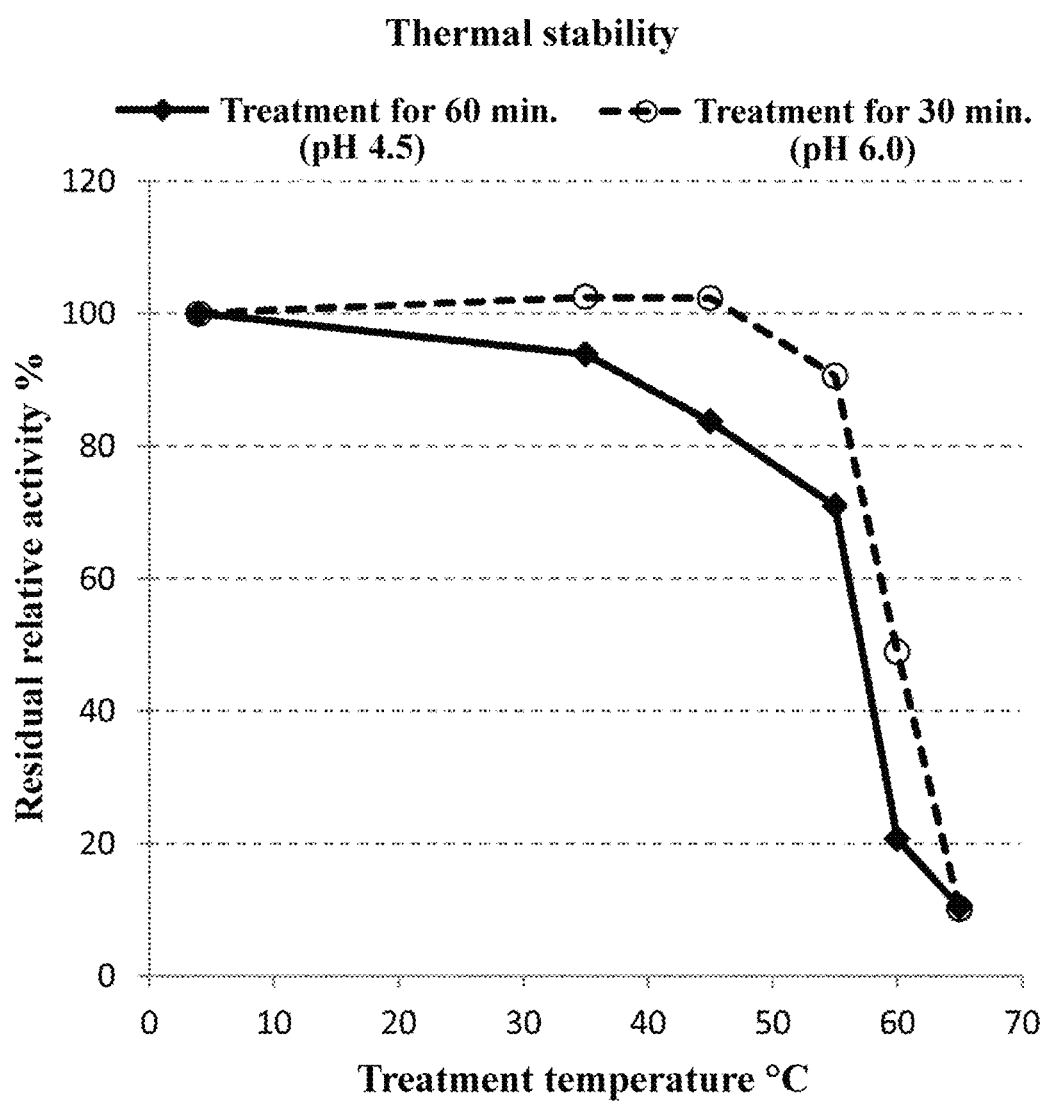
FIG. 14 Thermal stability of the purified enzyme (PN1).

The thermal stability of the nucleosidase of peak 3 collected from the DEAE HP column was analyzed. PN1 showed residual activity of 80% at up to 45° C. when treated at pH 4.5 for 60 minutes and at up to 55° C. when treated at pH 6.0 for 30 minutes (FIG. 14).

(3) Optimum pH

Figure 15:
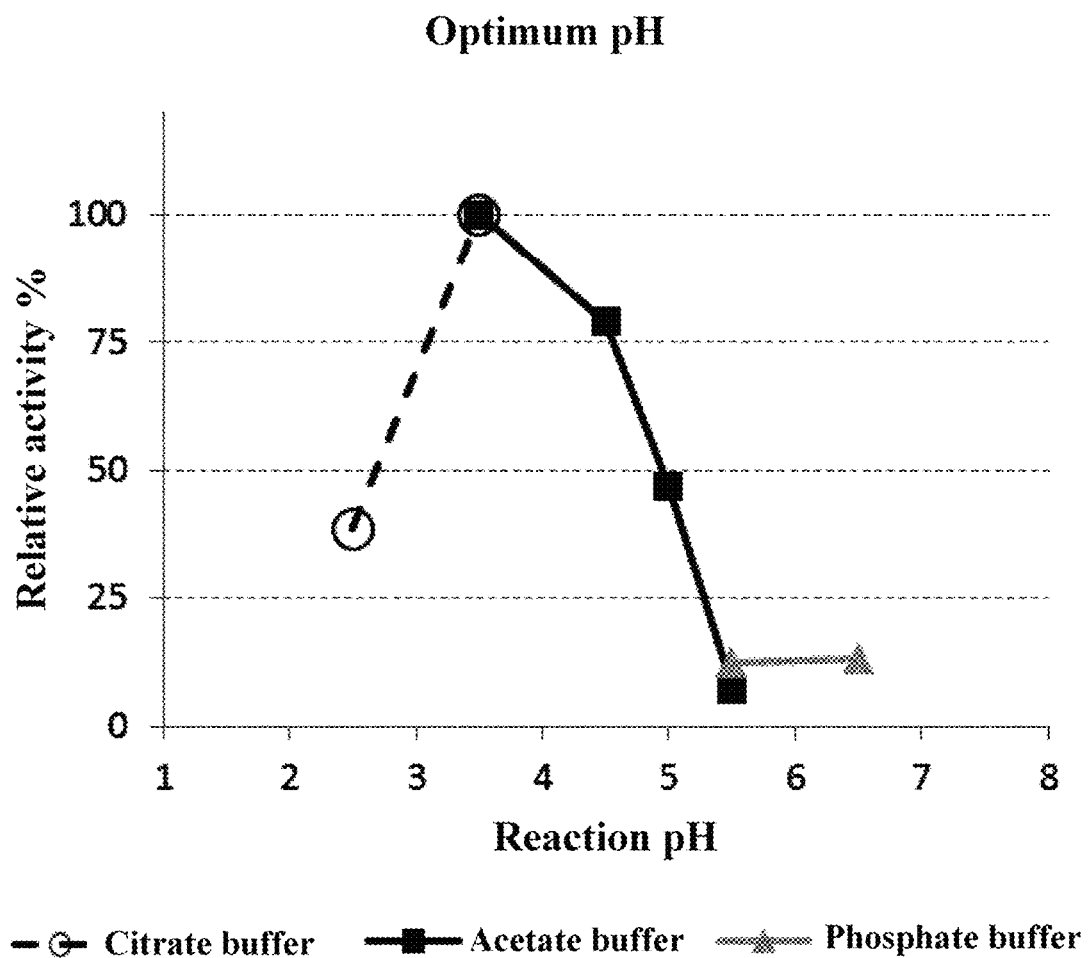
FIG. 15 Optimum pH of the purified enzyme (PN1).

The optimum pH of the nucleosidase of peak 3 collected from the DEAE HP column was analyzed. A citrate buffer was used for pH 2.5 and pH 3.5, an acetate buffer was used for pH 3.5, pH 4.5, and pH 5.5, and a potassium phosphate buffer was used for pH 5.5 and pH 6.5. The optimum pH was pH 3.5 (FIG. 15).

(4) pH Stability

Figure 16:
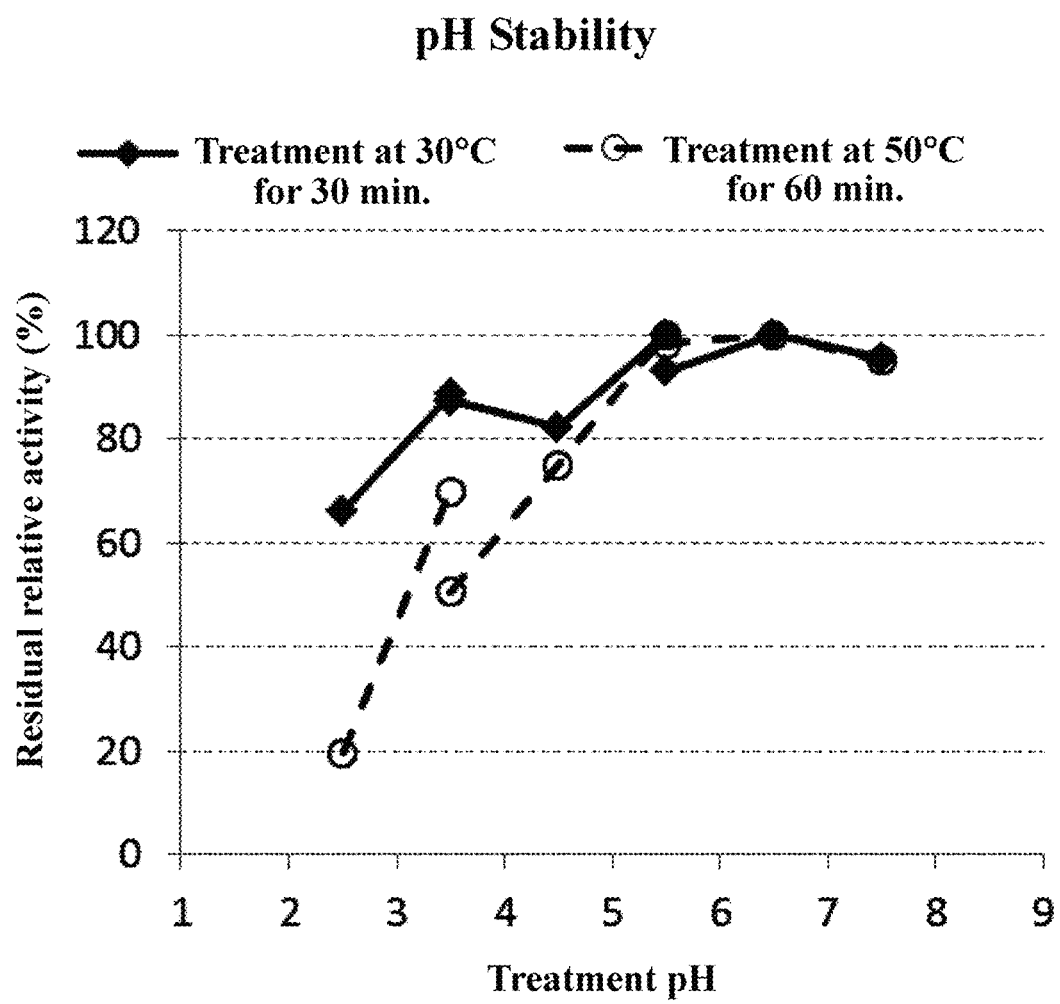
FIG. 16 pH stability of the purified enzyme (PN1).

The pH stability of the nucleosidase of peak 3 collected from the DEAE HP column was analyzed when treatment was carried out at 30° C. for 30 minutes and at 50° C. for 60 minutes, respectively, at each pH. The same buffers were used as those used for the study on the optimum pH, and a potassium phosphate buffer was used for pH 7.5. The nucleosidase showed residual activity of 80% or more at a pH of 3.5 to 7.5 when treated at 30° C. for 30 minutes and at a pH of 3.5 to 7.5 when treated at 50° C. for 60 minutes (FIG. 16).

4. Recombinant Production of Enzyme PN2

Figure 17:
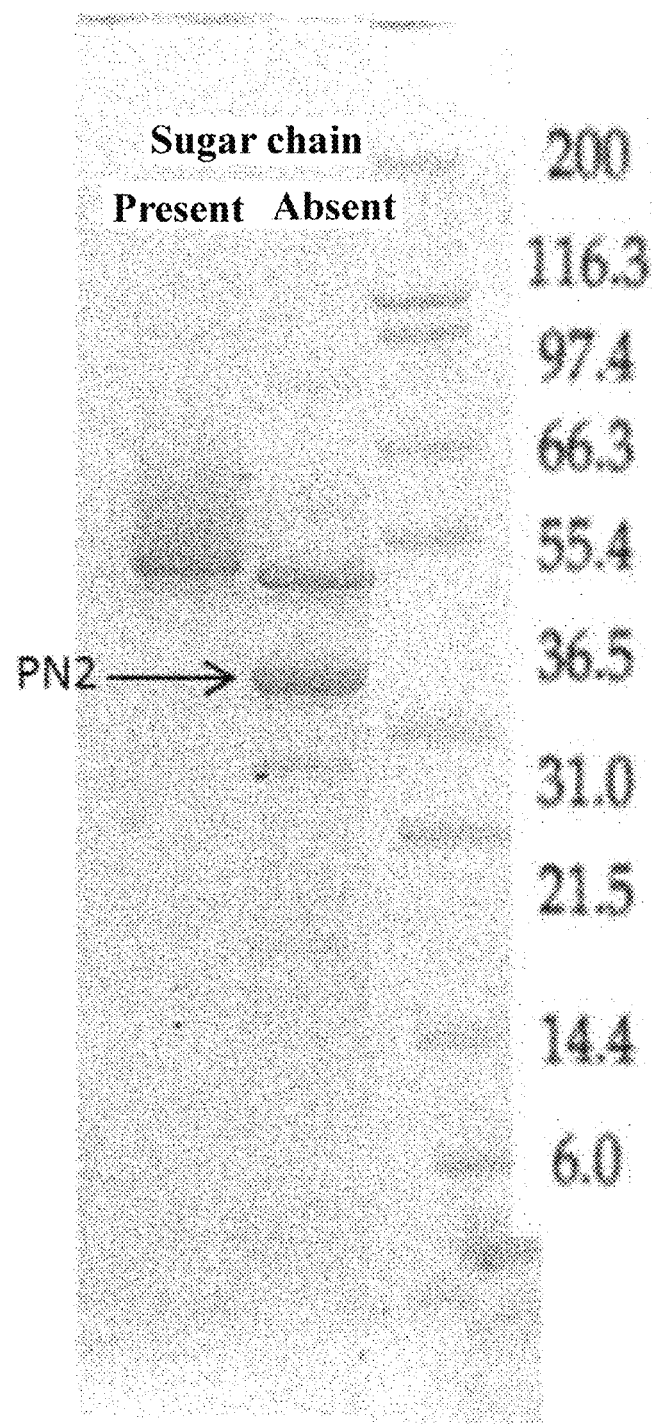
FIG. 17 Results of electrophoresis of the recombinantly produced enzyme (PN2).

The cDNA fragment of PN2 was inserted into the cloning site of an expression vector to construct a PN2 expression vector. The expression vector was used to transform Aspergillus oryzae (A. oryzae (pyrG-)). The obtained transformant was cultured in liquid for 4 days (30° C., 300 rpm). The culture supernatant was collected to measure the nucleosidase activity. As a result, it was revealed that a transformant showing activity was obtained. In addition, when the culture supernatant was subjected to sugar chain removal treatment and electrophoresis, a band having a size consistent with the estimated molecular weight was confirmed (FIG. 17).

5. Study on Various Properties of Enzyme PN2

Recombinantly produced PN2 was used to study various properties. Experiment method, conditions, and the like were the same as in the case of the study on PN1.

(1) Optimum Temperature

Figure 18:
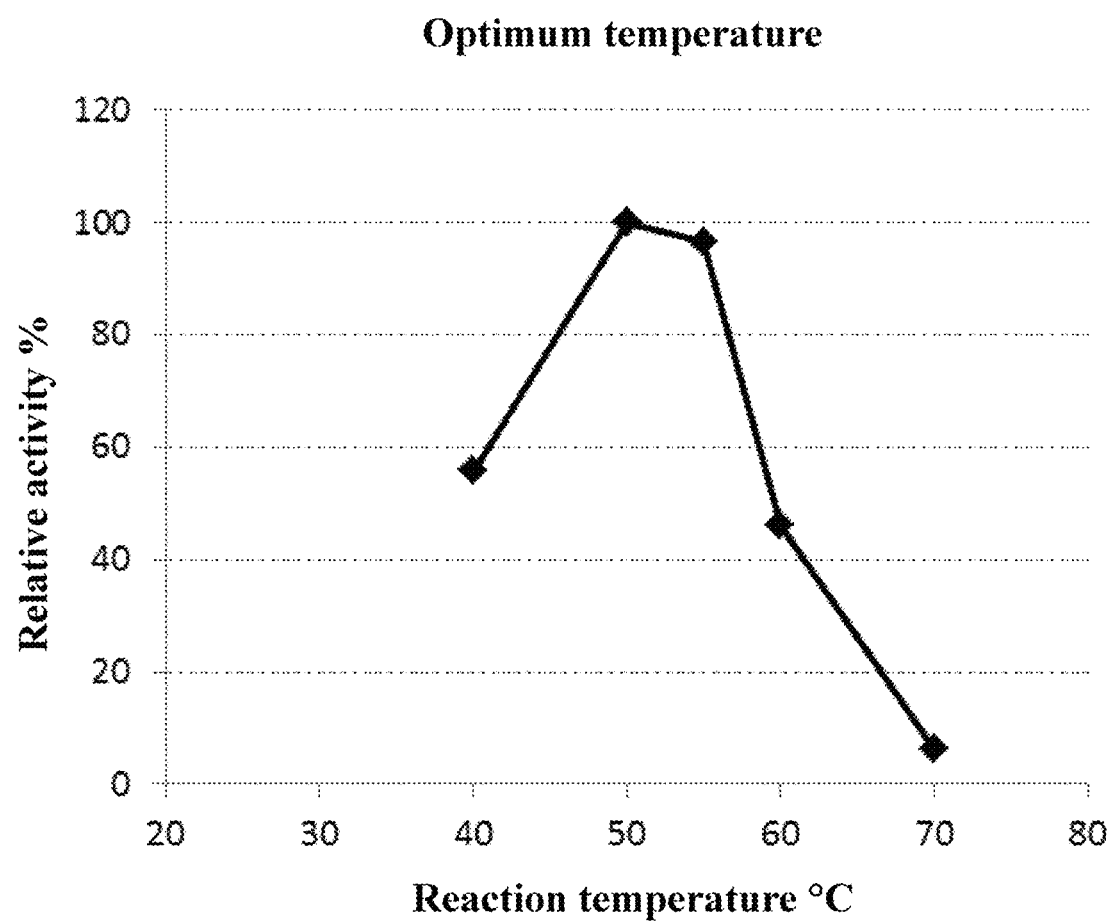
FIG. 18 Optimum temperature of the purified enzyme (PN2).

The optimum temperature was 50° C. to 55° C. (FIG. 18).

(2) Thermal Stability

Figure 19:
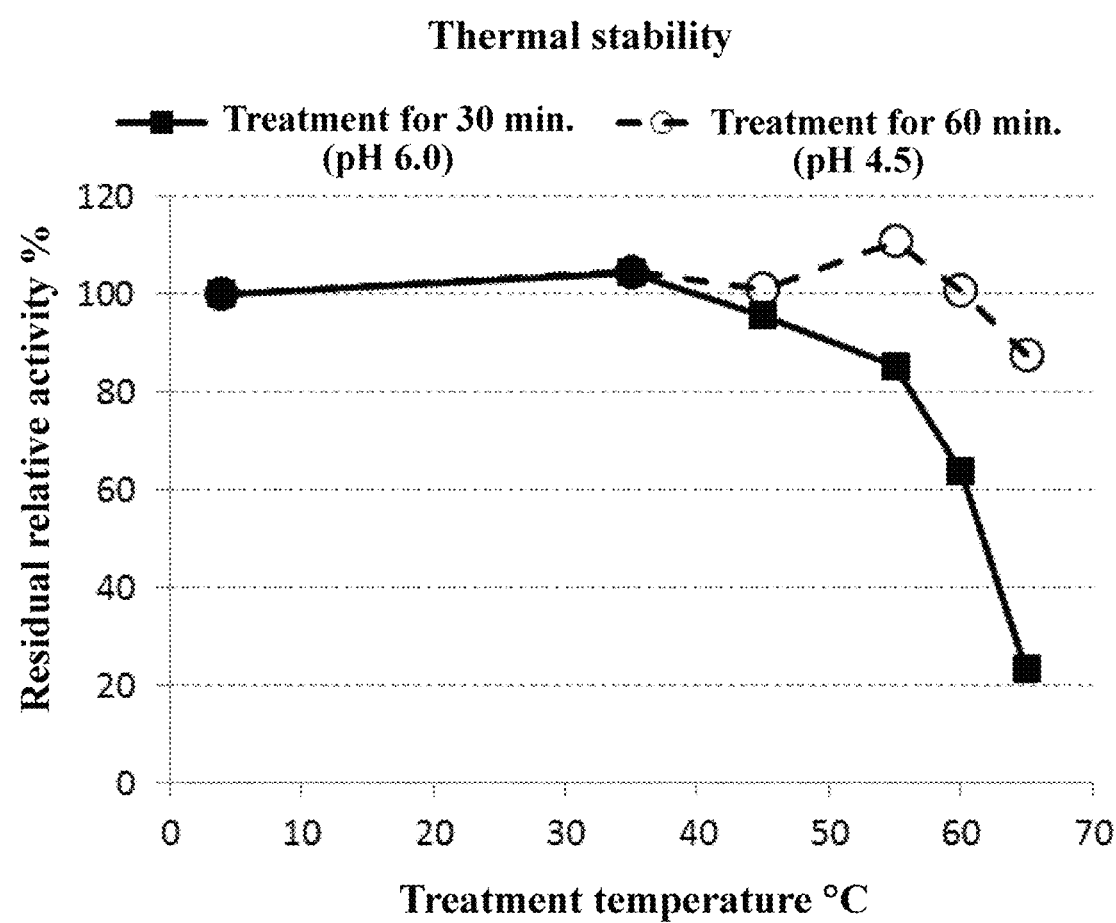
FIG. 19 Thermal stability of the purified enzyme (PN2).

PN2 showed residual activity of 80% at up to 65° C. when treated at pH 4.5 for 60 minutes and at up to 55° C. when treated at pH 6.0 for 30 minutes (FIG. 19).

(3) Optimum pH

Figure 20:
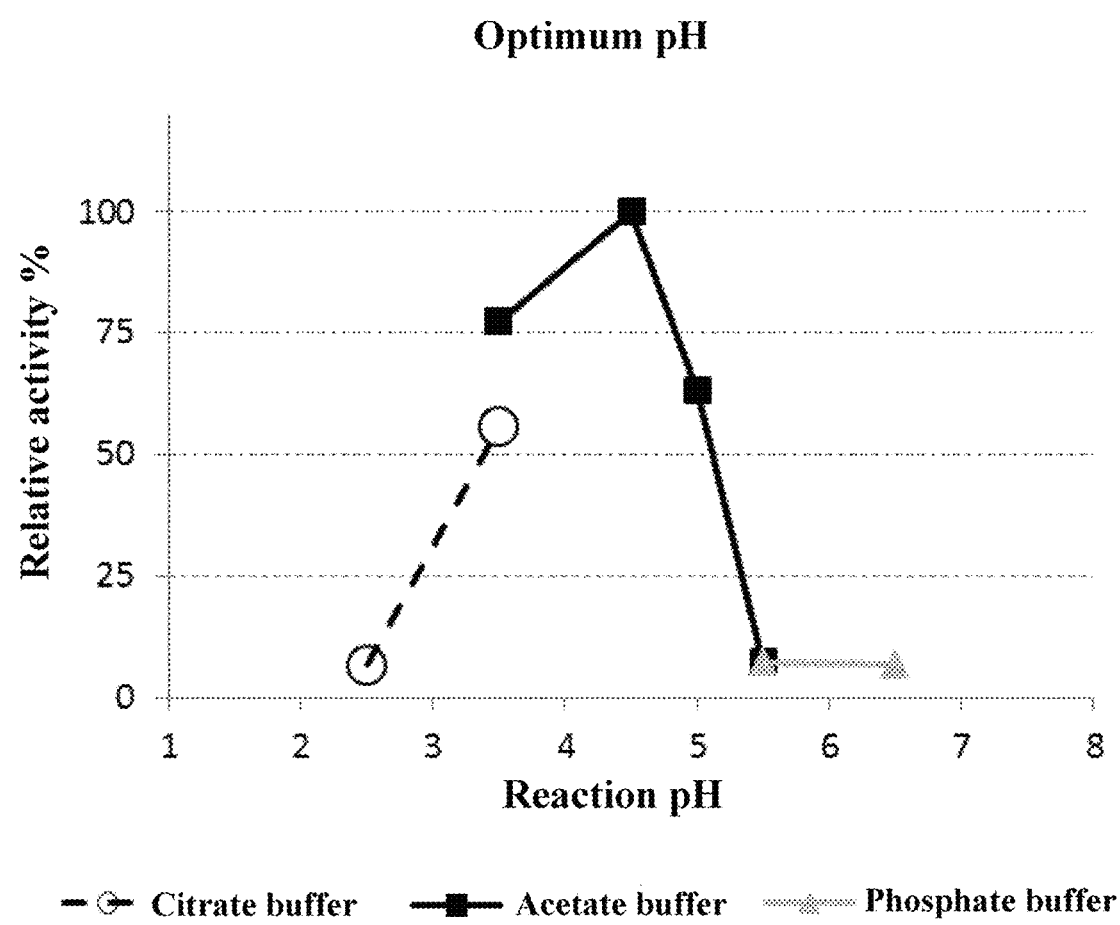
FIG. 20 Optimum pH of the purified enzyme (PN2).

A citrate buffer was used for pH 2.5 and pH 3.5, an acetate buffer was used for pH 3.5, pH 4.5, and pH 5.5, and a potassium phosphate buffer was used for pH 5.5 and pH 6.5. The optimum pH was 4.5 (FIG. 20).

(4) pH Stability

Figure 21:
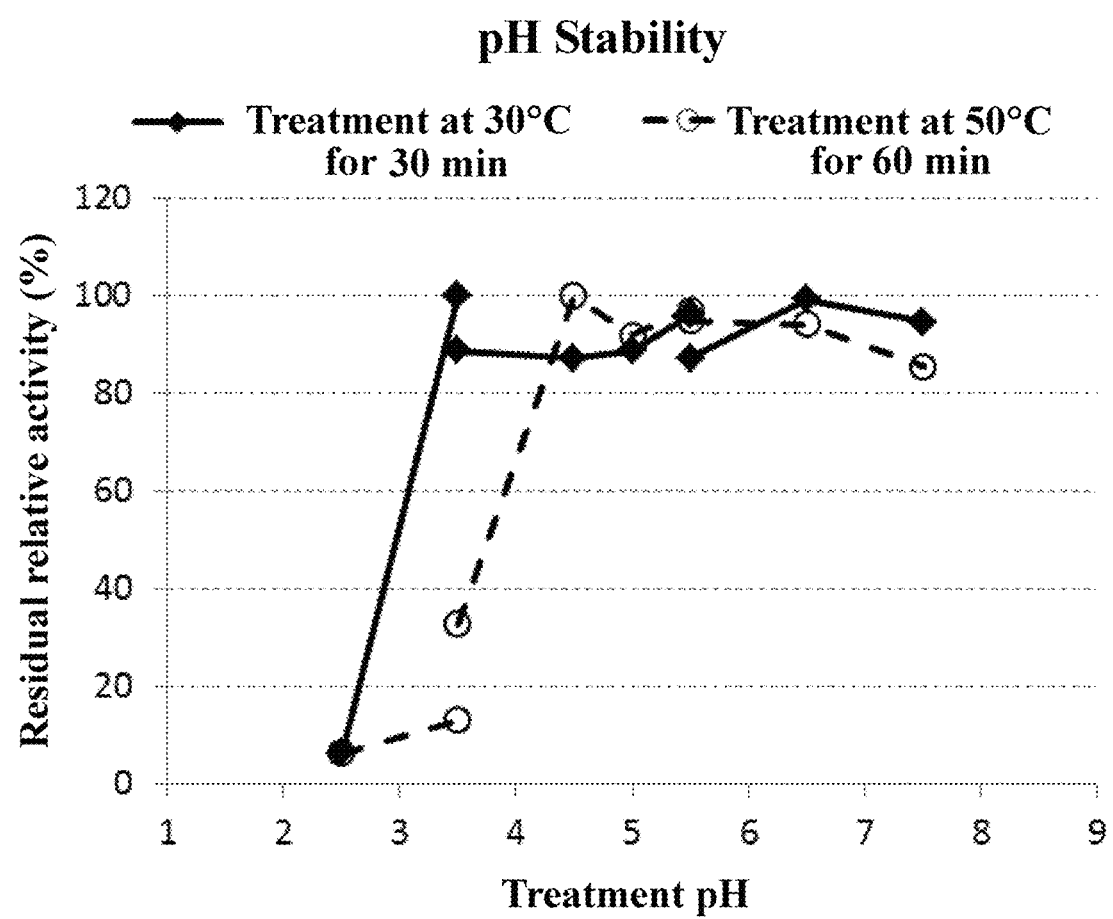
FIG. 21 pH stability of the purified enzyme (PN2).

The pH stability was analyzed when treatment was carried out at 30° C. for 30 minutes and at 50° C. for 60 minutes, respectively, at each pH. The same buffers were used as those used for the study on the optimum pH. PN2 showed residual activity of 80% or more at a pH of 3.5 to 7.5 when treated at 30° C. for 30 minutes and a pH of 4.5 to 7.5 when treated at 50° C. for 60 minutes (FIG. 21).

6. Mashing Test on Enzyme PN2

Figure 22:
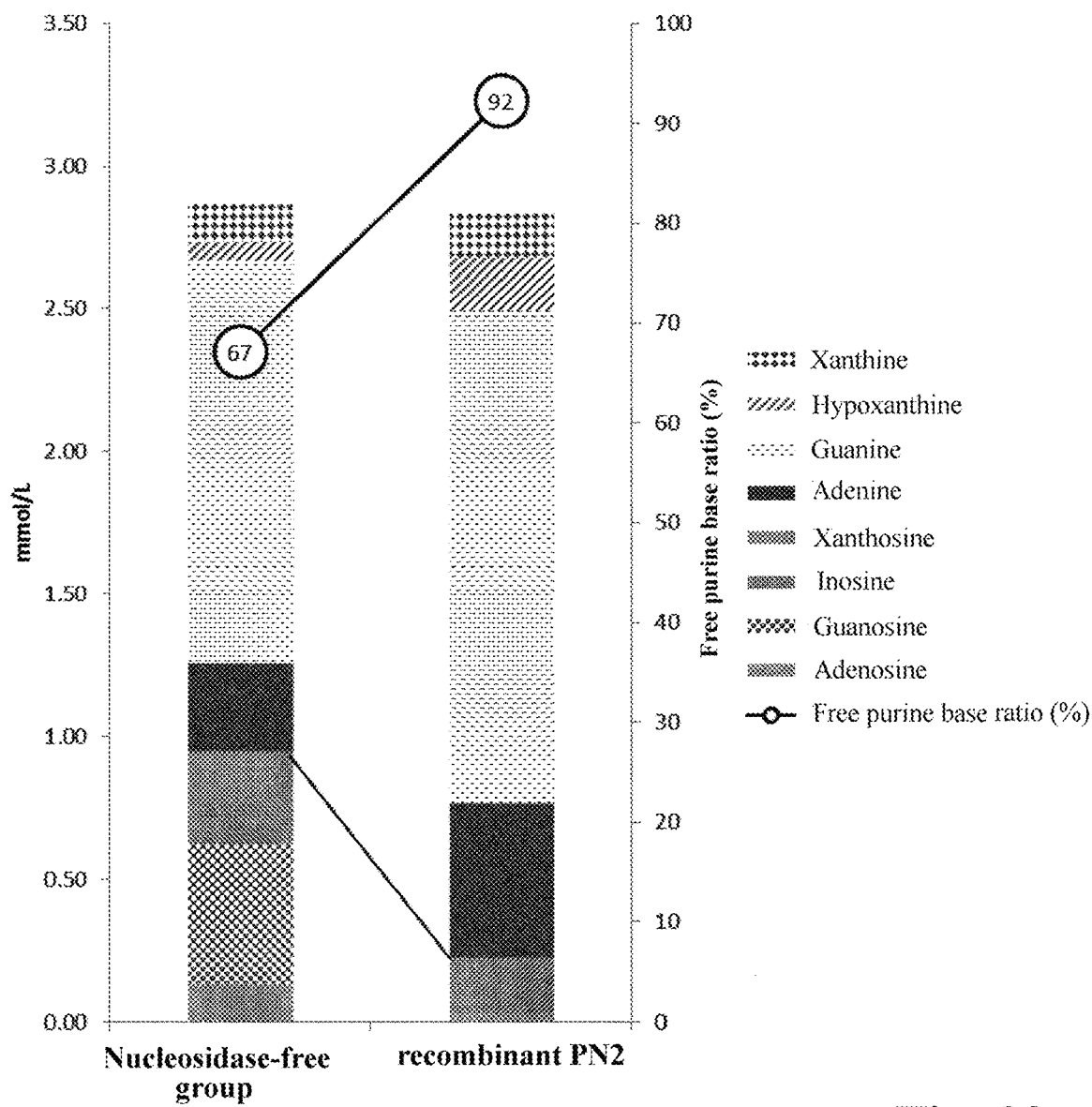
FIG. 22 Results of a mashing (preparation) test using the recombinantly produced enzyme (PN2).

A mashing test was conducted using recombinantly produced PN2. Test methods, conditions, and the like were the same as in the above 1. (4). The amount of each purine body in the wort after mashing was quantitatively analyzed by high performance liquid chromatography. The analysis results are shown in FIG. 22. It can be seen that, in the wort to which PN2 (nucleosidase) was added, the purine nucleosides decrease and the purine bases increase.

7. Mashing Test Under Low-pH Conditions

Figure 23:
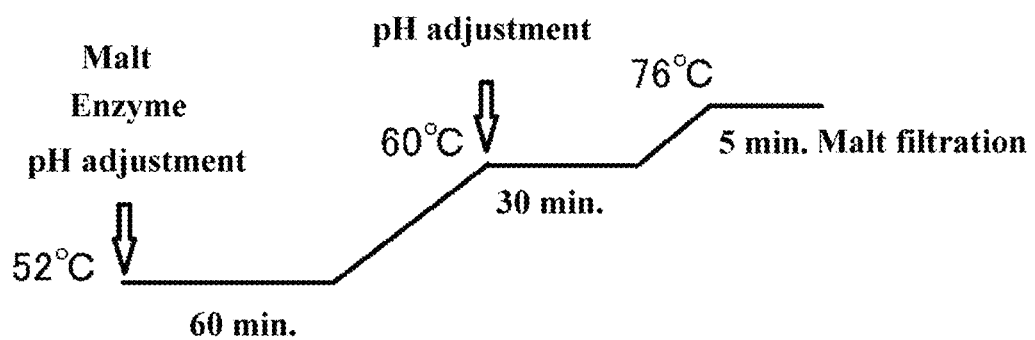
FIG. 23 Reaction process of the mashing (preparation) test.
Figure 24:
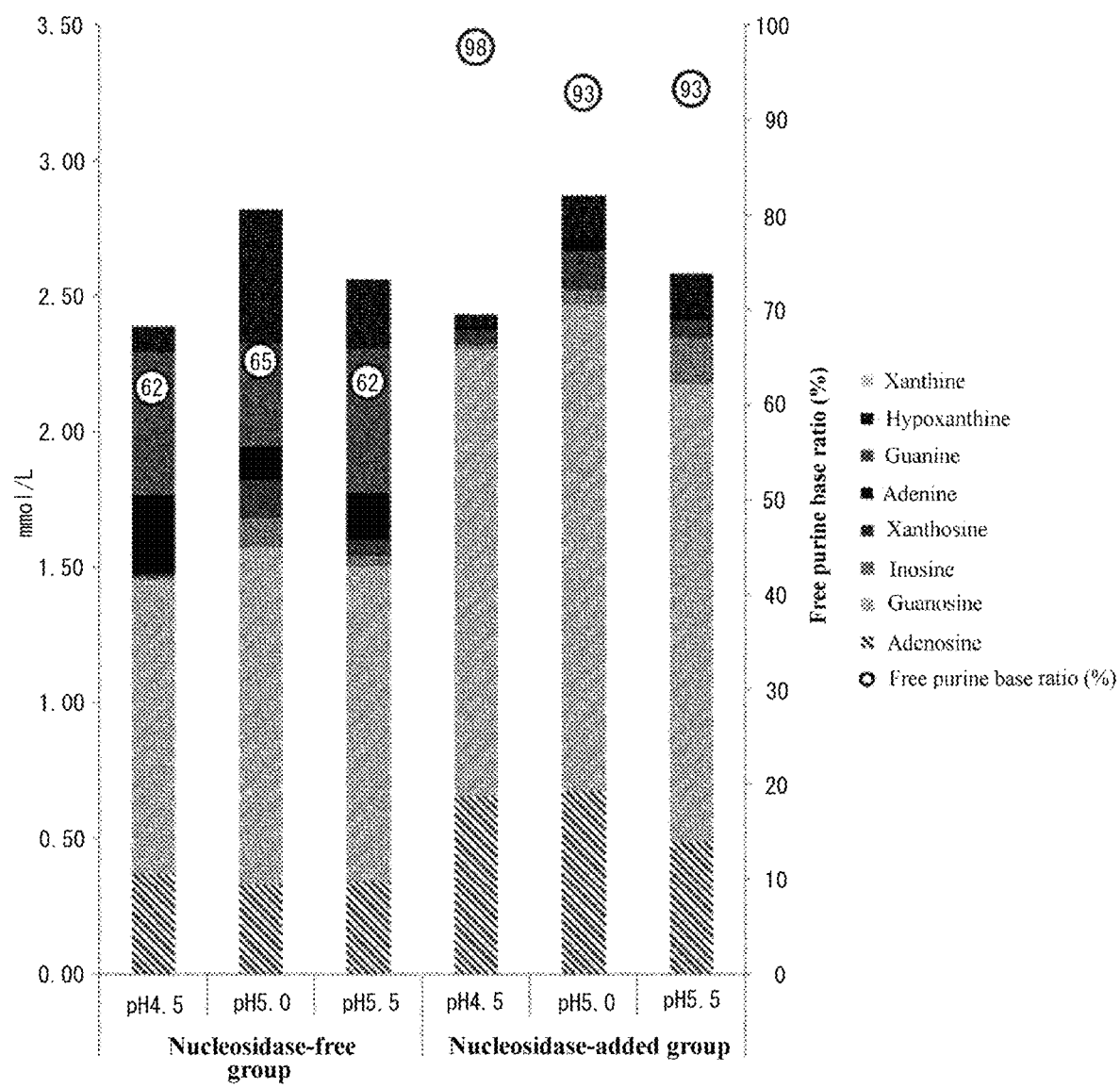
FIG. 24 Comparison in amounts of purine bodies in wort. The mashing test was carried out at a pH of 4.5 to 5.5. The amounts of the respective purine bodies in the wort after mashing were analyzed by high performance liquid chromatography.

In order to further confirm the usefulness of the nucleosidase derived from the Penicillium multicolor IFO 7569 strain in the production of beer or beer-based beverages, a mashing test was carried out at a pH around the optimum pH (pH 4.5 to 5.5) of the enzyme to study whether the desired effect (that is, reduction in purine bodies) could be obtained. Together with 80 g of pulverized malt and 320 mL of water, the nucleosidase was added in an amount equivalent to 2400 U, and the pH at the initial (52° C.) and 60° C. processes were each adjusted to pH 4.5, pH 5.0, or pH 5.5, and a mashing test was conducted to prepare wort. The reaction process is shown in FIG. 23. The amount of each purine body in the wort after mashing was quantitatively analyzed by high performance liquid chromatography under the following conditions. The analysis results are shown in FIG. 24. Even when mashing was carried out at a pH of 4.5 to 5.5, this nucleosidase had a free purine base ratio of 90% or more, and it can be seen that the purine nucleosides sufficiently decrease and the purine bases increase. (FIG. 24)

<HPLC Conditions>

Column: Asahipak GS-220 HQ

Mobile phase: 150 mM sodium phosphate buffer (pH 2.5)

Temperature: 35° C.

Flow rate: 0.5 mL/min

Detection: 260 nm

8. Conclusion

The nucleosidase derived from the Penicillium multicolor IFO 7569 strain showed an optimum temperature and thermal stability suitable for use in the beer preparation process. It was also found that the nucleosidase is excellent in pH stability and thermal stability, and can be applied not only to the production of beer or beer-based beverages but also to various uses. In this way, the inventors have succeeded in obtaining a novel nucleosidase extremely useful for reducing purine bodies in beverages and foods.

INDUSTRIAL APPLICABILITY

The nucleosidase of the present invention exhibits a characteristic feature of showing activity even in the presence of purine bodies of degradation products. The present invention can be used for producing low-purine foods or beverages such as low-purine beer and the like.

The present invention is not limited to the description of the embodiments and examples of the present invention at all. Various modifications that can be easily achieved by those skilled in the art without departing from the claims also fall within the scope of the invention. The contents of the articles, the patent laid-open publications, patent publications, and the like specified herein shall be cited by incorporation in their entity.

[Sequence Listing]

The invention claimed is:

1. A recombinant DNA comprising any DNA selected from the group consisting of the following (a) to (d):

(a) a DNA encoding the amino acid sequence of SEQ ID No: 1 or SEQ ID No: 2;

(b) a DNA encoding an amino acid sequence having 85% or more identity with the amino acid sequence of SEQ ID No: 1 or an amino acid sequence having 88% or more identity with the amino acid sequence of SEQ ID No: 2 and encoding a protein having nucleosidase activity;

(c) a DNA consisting of the base sequence of SEQ ID No: 3, or SEQ No: 5; and (d) a DNA having a base sequence equivalent to the base sequence of SEQ ID No: 3, equivalent to the base sequence of SEQ ID No: 4, equivalent to the base sequence of SEQ No: 5, or equivalent to the base sequence of SEQ ID No: 6, and wherein the DNA encodes a protein having nucleosidase activity.

2. A microorganism possessing the recombinant DNA according to claim 1.

3. A method for producing a nucleosidase, comprising the following steps (1) and (2):

(1) culturing a microorganism comprising a nucleosidase gene; wherein the encoded nucleosidase comprises the amino acid sequence of SEQ ID No: 1 or an amino acid sequence having 85% or more identity with the amino acid sequence of SEQ ID No: 1, or the amino acid sequence of SEQ ID No: 2 or an amino acid sequence having 88% or more identity with the amino acid sequence of SEQ ID No: 2 and (2) collecting the nucleosidase from the culture solution and/or the cell bodies after culture.

4. The production method according to claim 3, wherein the microorganism is a *Penicillium multicolor* IFO 7569 strain or a mutant strain thereof.

5. A method for producing a nucleosidase, comprising the following steps (i) and (ii):

(i) culturing the microorganism according to claim 2 under conditions where the nucleosidase encoded by the recombinant DNA is produced; and (ii) collecting the nucleosidase produced.

6. A method for producing a nucleosidase preparation, comprising the following steps (I) and (II):

(I) culturing a microorganism comprising a nucleosidase gene, wherein the encoded nucleosidase comprises the amino acid sequence of SEQ ID No: 1 or an amino acid sequence having 85% or more identity with the amino acid sequence of SEQ ID No: 1, or the amino acid sequence of SEQ ID No: 2 or an amino acid sequence having 88% or more identity with the amino acid sequence of SEQ ID No: 2; and (II) removing the cell bodies after culture.

7. The production method according to claim 6, further comprising the following step of (III) purifying the culture solution after removing the cell bodies.

8. The production method according to claim 6, wherein the microorganism is a *Penicillium multicolor* IFO 7569 strain or a mutant strain thereof.

* * * * *